(12) United States Patent
Arnold et al.

(10) Patent No.: US 10,030,220 B2
(45) Date of Patent: Jul. 24, 2018

(54) SINGLE-USE BIOREACTOR AND HEAD PLATE, AND A PROCESS FOR MANUFACTURING SAME

(71) Applicant: EPPENDORF AG, Hamburg (DE)

(72) Inventors: Matthias Arnold, Aachen (DE); Heinz Gerhard Kohn, Hamburg (DE); Nico Gulzow, Hamburg (DE); Sven Eikelmann, Petershagen (DE); Sebastian Selzer, Aachen (DE); Jochen Beese, Norderstedt (DE); Christopher Gunther, Hamburg (DE); Eckart Kopowski, Braunschweig (DE)

(73) Assignee: EPPENDORF AG, Hamburg (DE)

( * ) Notice: Subject to any disclaimer, the term of this patent is extended or adjusted under 35 U.S.C. 154(b) by 58 days.

(21) Appl. No.: 14/408,069

(22) PCT Filed: Jun. 13, 2013

(86) PCT No.: PCT/EP2013/062225
§ 371 (c)(1),
(2) Date: Dec. 15, 2014

(87) PCT Pub. No.: WO2013/186294
PCT Pub. Date: Dec. 19, 2013

(65) Prior Publication Data
US 2015/0132840 A1    May 14, 2015

Related U.S. Application Data

(60) Provisional application No. 61/660,554, filed on Jun. 15, 2012.

(30) Foreign Application Priority Data

Jun. 15, 2012   (EP) ..................................... 12172304

(51) Int. Cl.
C12M 1/00   (2006.01)
C12M 3/00   (2006.01)
C12M 1/06   (2006.01)

(52) U.S. Cl.
CPC ............ *C12M 23/28* (2013.01); *C12M 23/40* (2013.01); *C12M 23/42* (2013.01); *C12M 27/02* (2013.01);
(Continued)

(58) Field of Classification Search
CPC ...... C12M 27/00; C12M 27/02; C12M 27/08; B01L 3/50; B01L 3/50853
See application file for complete search history.

(56) References Cited

U.S. PATENT DOCUMENTS 8,746,515 B2   6/2014 Fatherazi et al.
9,044,718 B2   6/2015 Ludwig et al.
(Continued)

FOREIGN PATENT DOCUMENTS

CN      1392241 A      1/2003
CN    101886039 A     11/2010
(Continued)

OTHER PUBLICATIONS

Chinese Examination Report and English translation for related Chinese Patent Application No. 201380031555.6, issued Sep. 14, 2015.
(Continued)

*Primary Examiner* — Nathan A Bowers
(74) *Attorney, Agent, or Firm* — Merchant & Gould P.C.

(57) ABSTRACT

A single-use bioreactor, suitable in particular for use in a parallel bioreactor system for applications in cell culture and/or microbiology, a head plate for such a single-use bioreactor and a process for manufacturing the single-use bioreactor and the head plate. The single-use bioreactor (Continued)

Figure 1A:
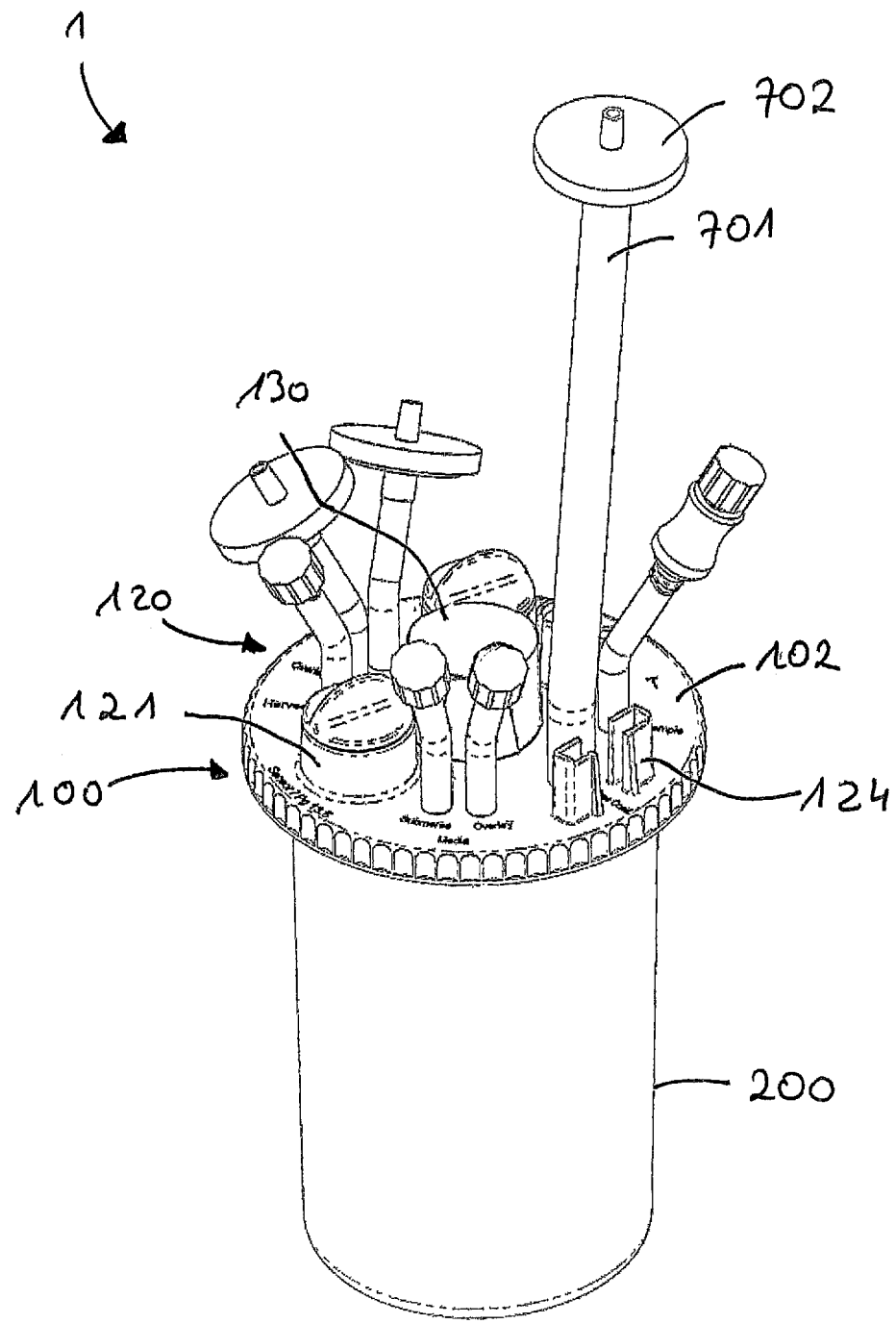

comprises a head plate, a dimensionally stable container and a mixer, the head plate and the container enclosing a reaction chamber, and the mixer having a mixer shaft and a stirring member, said mixer shaft being mounted rotatably about a rotational axis in a bearing and the stirring member being fastened torsionally rigidly to the mixer shaft. The mixer and the bearing are arranged entirely within the reaction chamber and the mixer shaft has a magnetic portion which is arranged and adapted in such a way that it can be coupled magnetically in an axial direction to a rotary drive.

12 Claims, 17 Drawing Sheets

(52) U.S. Cl.
CPC ........ *Y10T 29/49826* (2015.01); *Y10T 156/10* (2015.01)

(56) References Cited

U.S. PATENT DOCUMENTS

| | | |
|---|---|---|
| 2007/0253288 A1 | 11/2007 | Mennega et al. |
| 2008/0131957 A1 | 6/2008 | Ryan et al. |
| 2009/0035856 A1* | 2/2009 | Galliher ................ C12M 23/14 435/383 |
| 2009/0152744 A1 | 6/2009 | Mou |
| 2010/0291674 A1 | 11/2010 | Beese et al. |
| 2011/0003374 A1* | 1/2011 | Van Den Boogaard ............ B01F 7/1695 435/289.1 |
| 2011/0058447 A1 | 3/2011 | Reif et al. |
| 2011/0058448 A1 | 3/2011 | Reif et al. |
| 2011/0207170 A1 | 8/2011 | Niazi |

FOREIGN PATENT DOCUMENTS

| | | |
|---|---|---|
| CN | 101977673 A | 2/2011 |
| DE | 202007005868 U1 | 7/2007 |
| DE | 10 2008 027 638 | 12/2009 |
| DE | 202010007640 U1 | 8/2010 |
| DE | 10 2009 056 468 | 6/2011 |
| DE | 20 2009 015 434 | 5/2012 |
| EP | 2 065 085 | 6/2009 |
| EP | 2 251 407 | 11/2010 |
| EP | 2251407 A1 | 11/2010 |
| JP | 2009-543553 A | 12/2009 |
| JP | 2010-263891 A | 11/2010 |
| WO | WO 03/006633 | 1/2003 |
| WO | WO 2007/134267 | 11/2007 |
| WO | 2008/088379 A2 | 7/2008 |
| WO | WO 2008/088379 | 7/2008 |
| WO | WO 2009/009771 | 1/2009 |
| WO | 2010/108091 A2 | 9/2010 |

OTHER PUBLICATIONS

International Search Report and Written Opinion for International Application No. PCT/EP2013/062225 dated Jul. 19, 2013 (24 pages).
Japanese Office Action from related Japanese Patent Application No. 2015-516610, dated Aug. 16, 2016, 7 pages.
Office Action from related Chinese Patent Application No. 201380031555.6, dated Aug. 16, 2016.

* cited by examiner

A-A

500
SINGLE-USE BIOREACTOR AND HEAD PLATE, AND A PROCESS FOR MANUFACTURING SAME

This application is a National Stage Application of PCT/EP2013/062225, filed 13 Jun. 2013, which claims benefit of U.S. Provisional Ser. No. 61/660,554, filed 15 Jun. 2012, and European Application No. 12172304.3, filed 15 Jun. 2012, and the entire disclosure of these applications are incorporated herein by reference. To the extent appropriate, a claim of priority is made to each of the above disclosed applications.

The invention relates to a single-use bioreactor suitable in particular for use in a preferably parallel bioreactor system for applications in cell culture and/or microbiology, comprising a head plate, a dimensionally stable container and a mixer, wherein the head plate and the container enclose a reaction chamber, the head plate having an inner side facing towards the reaction chamber, and an outer side which faces away from the reaction chamber and which has a plurality of connectors, and the mixer having a mixer shaft and a stirring member, the mixer shaft being mounted rotatably about a rotational axis in a bearing and the stirring member being attached torsionally rigidly to the mixer shaft.

The invention also relates to a head plate for a single-use bioreactor suitable in particular for use in a preferably parallel bioreactor system for applications in cell culture and/or microbiology.

The invention further relates to a process for manufacturing a single-use bioreactor suitable in particular for use in a preferably parallel bioreactor system for applications in cell culture and/or microbiology and to a process for manufacturing a head plate for a single-use bioreactor suitable in particular for use in a preferably parallel bioreactor system for applications in cell culture and/or microbiology.

BACKGROUND OF THE INVENTION

Bioreactors, which are also frequently referred to as fermenters, enclose a reaction chamber in which biological or biotechnological processes can be carried out on a laboratory scale. Such processes include, for example, the cultivation of cells, microorganisms or small plants under defined, preferably optimized, controlled and reproducible conditions. Bioreactors mostly have a plurality of connectors via which the primary and secondary substances, as well as various instruments, such as sensors, can be introduced to the reaction chamber or to which fluid conduits, for example, in particular gas conduits such as gassing conduits or exhaust gas conduits, can be connected. In addition, bioreactors generally include a mixer, the shaft of which can be made to rotate by a drive, as a result of which a stirring member connected torsionally rigidly to the mixer shaft is likewise made to rotate, thus mixing the substances present in the reaction chamber. It is also possible for two or more stirring members, mostly spaced axially apart, to be arranged on and connected to the mixer shaft. The stirring member or stirring members may also be integral with the mixer shaft.

Bioreactors are preferably used in bioreactor systems, preferably in parallel bioreactor systems, not only in the field of cell cultivation but also in microbiological applications. Parallel bioreactor systems are described in DE 10 2011 054 363.5 and DE 10 2011 054 365.1, for example. In such bioreactor systems, a plurality of bioreactors can be operated in parallel and controlled with higher precision. High-throughput experiments that are well reproducible and scalable can be carried out in the individual bioreactors, even with small operating volumes. The laboratory scale of the bioreactors to which the invention relates involves volumes of up to 2000 ml, or more specifically with a total reaction chamber volume of approximately 350 ml, with a working volume ranging between about 60 ml and about 250 ml.

In the cell culture field, such parallel bioreactor systems are used, for example, for test series for process optimization based on statistical planning methods (design of experiments DoE), for process engineering and in research and development, for example to cultivate different cell lines such as Chinese hamster ovary (CHO), hybridoma or NS0 cell lines. In the context of the present application, the expression "cell culture" is specifically understood to mean the cultivation of animal or plant cells in a nutrient medium outside the organism.

In the field of microbiology, parallel bioreactor systems are likewise used for test series for process optimization based on statistical planning methods (design of experiments DoE), for process engineering and in research and development, for example to cultivate various microorganisms, in particular bacteria or fungi, such as yeast.

Due to limitations of space in most laboratories, minimal space requirements and in particular small footprints are striven for, not only for bioreactor systems but also for the bioreactors themselves.

Bioreactors used in laboratories are often made of glass and/or metal, in particular of stainless steel, as the bioreactors must be sterilized between different uses, preferably by steam sterilization in autoclaves. Sterilizing and cleaning reusable bioreactors is a complex process. The sterilization and cleaning process can be subject to validation, and needs to be precisely documented for each individual bioreactor. Residues in a bioreactor which has not been fully sterilized can falsify the results of a subsequent process, or render them useless, and may cause disruption of the subsequent process. Furthermore, the sterilization process may also expose Individual components or materials in bioreactors to stress and strain, and in some cases can damage them.

Single-use bioreactors provide an alternative to reusable bioreactors and are used to carry out just one biological or biotechnological process before being disposed of. By providing a new single-use bioreactor for each process, and one that is preferably sterilized during the production process, it is possible to reduce the risk of (cross-)contamination, while simultaneously obviating the need to perform and document the impeccable cleaning and sterilization of a previously used bioreactor. Single-use bioreactors are often designed as flexible containers, for example as bags, or as containers having walls that are flexible in sections thereof at least. Examples of such bioreactors are described in US 2011/0003374 A1, US2011/0058447A1, DE 20 2007 005 868U1, US 2011/0058448A1, US2011/0207218A1, WO 2008/088379A2, US 2012/0003733 A1, WO2011/079180A1, US2007/0253288A1, US 2009/0275121A1 and US 2010/0028990A1. However, one disadvantage of these single-use bioreactors with flexible walls, inter alia, is that they cannot be used in parallel bioreactor systems, which are designed for dimensionally stable, reusable bioreactors.

Further, for reasons of scalability of processes to different scale, qualitative comparable and particularly defined fluid dynamics (particularly during stirring) in the cultivation chamber are important, This requirement cannot be realized with bioreactors with flexible walls or can be realized only with extensive additional measures.

Dimensionally stable single-use bioreactors are known from EP 2 251 407 A1 and from US 2009/0311776 A1, for example. Examples of dimensionally stable single-use bioreactors available on the market include the Celligen Blu, the Millipore Mobius and the Sartorius UniVessel. However, these known, dimensionally stable single-use bioreactors are high-priced, on the one hand, and on the other hand are designed for pharmaceutical process engineering and pharmaceutical production processes. These are used for cell culture processes, in particular, and are therefore specifically designed and adapted for such cell culture processes. Different requirements must be met for applications in microbiology, however, not only with regard to the prices that can be charged on the market, but also with regard to appropriate design and to the materials that can be used. Dimensionally stable single-use bioreactors known from the prior art are unsuitable, therefore, for use in microbiology research or in process engineering, for example.

The object of the present invention is therefore to provide an improved single-use bioreactor and a head plate, and to specify a manufacturing process that reduces or eliminates one or more of the aforementioned disadvantages. One object of the present invention, more specifically, is to provide an improved single-use bioreactor which is suitable for use in both cell culture and microbiology applications, and in particular for use in a preferably parallel bioreactor system. Other objects of the invention are to provide a single-use bioreactor and a head plate which are inexpensive to produce, and to specify simple and cost-efficient processes for manufacturing a single-use bioreactor and a head plate.

SUMMARY OF THE INVENTION

According to a first aspect of the invention, these objects are achieved by a single-use bioreactor according to claim 1. This single-use bioreactor of the kind initially specified is characterized in that the mixer and the bearing are arranged entirely within the reaction chamber and that the mixer shaft has a magnetic portion, which is arranged and adapted in such a way that it can be coupled magnetically in an axial direction to a rotary drive. Since the rotary drive drives the mixer with a mixer shaft and a stirring member it is also referred to as stirring drive.

This single-use bioreactor is characterized, inter alia, in that the mixer can be made to rotate by a magnetic drive. One advantage of this embodiment is that both the mixer and the bearing are entirely arranged in the reaction chamber, i.e. that the mixer shaft does not have to be passed through the head plate. This also obviates the need to seal the hole through which the mixer shaft is passed through the head plate. This has the advantage that the sterility of the reaction chamber cannot be compromised as a result of a hole in the head plate being inadequately sealed. A further advantage is that frictional resistance occurring in constructions with sealed passage, which can lead, inter alia, to damage of septum components, are fully avoided.

It is further envisaged that a magnetic portion of the mixer shaft is magnetically coupled in an axial direction, i.e. in the direction of, or parallel to the axis of rotation, to a drive arranged outside the reaction chamber on the outer side of the head plate. A minimal air gap is preferably formed between a magnetic portion of the mixer shaft and a magnetic drive portion of the rotary drive. Such magnetic coupling at the front end between the mixer shaft and the rotary drive has the advantage that only little space is needed on the head plate for the rotary drive, compared to a coupling in the radial direction, in which a magnetic portion of the rotary drive is arranged around the outer periphery of a magnetic portion on the mixer shaft, as described for example in US 2011/0058447 A1. A rotary drive with a magnetic coupling at the front end can be substantially cylindrical in shape, for example, wherein the cross-sectional area of the cylinder may be substantially equal to the area required for the front-end magnetic coupling. More space thus remains on the head plate for arranging additional connections for instruments, sensors or functional elements.

In order to receive the magnetic portion of the mixer shaft, the head plate may have a convex portion, for example, which can have a circular cross-section, for example, and which can cradle a rotary drive arranged outside the reaction chamber by means of a ring, for example, in order to arrange the rotary drive concentrically over the convexity and the magnetic portion of the mixer shaft which preferably is likewise arranged concentrically therein. The magnetic portion of the mixer shaft is preferably arranged at one end of the mixer shaft and preferably has a larger diameter or a larger circumference than a remaining portion of the mixer shaft.

In one preferred embodiment, the magnetic portion is integrally embodied with the mixer shaft. This has the advantage that the number of parts in the reaction chamber is reduced and hence also that any potential gaps and dead spots between different parts are reduced.

It is particularly preferred that the magnetic portion consists of a composite material comprising a plastic matrix and a magnetic material, or includes such a composite material. This has the advantage that a combination of materials can be chosen which conforms to the United States Pharmacopeia (USP) Class VI requirements, for example by selecting a suitably classified plastic as the matrix.

It is also preferable that the magnetic portion is manufactured by injection molding the two-component material having a magnetic component onto the mixer shaft.

By injection molding such a plastic/magnet mixture as a composite material onto one end of the mixer shaft, preferably in an injection molding process, it is possible to manufacture the mixer shaft with a magnetic coupling portion at the front end in a particularly simple and inexpensive manner, which simultaneously reduces the number of parts in the reaction chamber due to the integral embodiment.

In one particularly preferred embodiment, the magnetic portion has a cross-section in a plane which is orthogonal to the mixer shaft, and exerts a magnetic force over the major part of said cross-section, preferably over the entire cross-section, for a magnetic coupling to a rotary drive in the axial direction.

Such a configuration of a preferably two-dimensional, contiguous cross-section of the region exerting a magnetic force may be achieved, more specifically, by injection molding a composite material comprising a plastic matrix and a magnetic material into an injection mold, which for its part contains a magnet for aligning the magnetic material of the composite during injection molding. The cross-section of the magnetic portion exerting magnetic force is preferably circular, ellipsoidal or rectangular. Within this cross-section of the magnetic portion exerting magnetic force, segments of differing polarity are preferably formed. For example, the segments may form a star-shaped pattern or a pattern with pie-shaped segments.

Such a configuration has several advantages. Firstly, a higher torque can be transmitted compared to an embodiment comprising a plurality of annularly arranged bar magnets. This is required, in particular, to achieve a higher rotor speeds in excess of 1500 rpm, in particular up to 2000 rpm, or up to 3000 rpm and more, speeds that are needed for applications in microbiology, in particular. It is possible at the same time to keep the required cross-sectional area at the end of the mixer shaft and hence the required construction space on the head plate small or low. By forming specific segment polarity patterns, it is possible to match bioreactors specifically to a correspondingly designed rotary drive and thus to increase the level of process reliability, since only bioreactors with matching segment polarities can be driven by a rotary drive. This is advantageous for ensuing that the drive has the desired torque and the desired speed, since torque and particularly the speed obtained are only monitored for mixers mechanically coupled to a rotational drive, however, not for magnetic coupling between mixer and rotational drive. A divergent speed, however, can exert a negative influence on the cultivation process, for example when using a rotary drive with too low a power rating.

Also in this embodiment the magnetic portion can be integrally connected with, preferably an end of, the mixer shaft, for example by injection molding of the composite material onto the mixing shaft. Alternatively, the magnetic portion can be made, preferably by an injection molding process, as a separate part and arranged on the mixer shaft.

According to a second aspect of the invention, the objects are achieved by a single-use bioreactor according to claim 4. According to this second aspect of the invention, the single-use bioreactor of the kind initially specified or a single-use bioreactors according to the first aspect of the invention, is characterized in that the bearing is designed as a roller bearing.

One disadvantage of the sliding bearings used in known, dimensionally stable single-use bioreactors for applications in cell culture is that the rotor speeds of the mixer are limited to ranges around approximately 500 rpm, since higher rotor speeds generate waste heat due to strong frictional forces between the shaft and the bearing, which can then lead to the bearing melting and thus to the shaft coming to a standstill, which would terminate the cultivation process. Another disadvantage of sliding bearings is the intensified abrasion of material, in particular abrasion of plastic material, which would provide an undesirable nuclei for cell agglomeration in the reaction chamber and which must therefore be captured in a bearing housing, for example.

By designing the bearing for the mixer shaft as a roller bearing, it is possible to achieve significantly higher speeds of more than 1500 rpm, in particular speeds of up to 2000 rpm, or up to 3000 rpm and more, which are speeds needed for applications in microbiology.

It is particularly preferred that the roller bearing is a polymer roller bearing with glass ball bearings, the polymer roller bearing preferably comprising a ball race made of a thermoplastic plastic, for example of polyethylene, polypropylene, polyvinylidene fluoride, polyether ether ketone or polytetrafluoroethylene. One advantage of this combination of materials for the roller bearing is that the glass ball bearings can run smoothly and quietly in the polymer roller bearing and can thus lower the noise level in the laboratory. This combination of materials is also resistant against alkalis and bases with high molarities, which are used in microbiological applications, in particular, and which therefore impose respective requirements with regard to construction and the materials deployed.

According to a third aspect of the invention, the obejctives are achieved by a single-use bioreactor according to claim 5. According to this aspect, the single-use bioreactor of the kind initially specified, or one of the previously described single-use bioreactors according to the first or second aspect of the invention is characterized in that the head plate and the container are permanently joined to each other, the head plate being formed of a first material and the container of a second material, and the mixer shaft and/or the stirring member being formed of a third material, the first material and the second material having a higher temperature resistance than the third material.

In this single-use bioreactor, the head plate and the container are permanently joined to each other, for example by a inseparable, integral joining technique such as welding. Joining by ultrasonic welding is particularly preferred, as this technique provides a high level of process reliability and results in excellent sealing of the connection between the head plate and the reaction chamber and hence in good sealing of the reaction chamber against its surroundings. Ultrasonic welding is also a very fast joining technique and reduces production cost and effort.

A permanent join between the head plate and the container has the advantage that the single-use bioreactor can no longer be opened after sterilization in the production process, and hence that the risk of the reaction chamber becoming contaminated prior to use of the single-use bioreactor can be reduced. This permanent join also has also the advantage that the single-use bioreactor cannot be opened after use, either, and that it retains its closed, dimensionally stable shape.

The advantages of the combination of materials according to the invention also become evident in connection with the decontamination of used single-use bioreactors. Single-use bioreactor made of material with a lower temperature-resistance have the disadvantage that they are damaged, e.g. melt, during decontamination or post-process sterilization and therefore need to be sterilized in a, preferably temperature-resistant, outer container. Making the head plate and the container from materials having a temperature resistance that permits decontamination, i.e. which are not destroyed or significantly attacked during decontamination, has the advantage that the single-use bioreactor can be decontaminated by steam sterilization, for example, without the single-use bioreactor having to be additionally packaged or disposed inside another container, since the head plate and the container can withstand this decontamination process.

The combination with a mixer shaft and/or a stirring member made of a material with a lower temperature resistance produces the advantage that the mixer shaft and/or the stirring member are destroyed or at least rendered unusable in the decontamination process. The third material has properties appropriate for that purpose. In particular, it is preferred that the third material has a temperature resistance which prevents it from withstanding a decontamination process.

It is possible in this way to prevent intentional or inadvertent re-use of a single-use bioreactor which has already been used once, since the mixer can no longer be used after decontamination, nor can the single-use bioreactor be opened to replace the mixer, due to the permanent join between the head plate and the container.

Another particularly preferred embodiment is one in which the first material of the head plate and the second material of the container are the same, which is specifically advantageous when ultrasonic welding is used as the method for joining the head plate and the container.

The temperature resistance of materials is defined here preferably as their glass transition temperature.

It is particularly preferred that the first material and the second material have a higher glass transition temperature than the third material. The glass transition temperature (Tg)

is a specific property of plastic materials. It refers to the temperature at which the amorphous or partially crystalline polymers transition from the solid state to the fluid state, which involves a significant change in physical characteristics, such as hardness and elasticity.

It is particularly preferred that the first material and the second material have a glass transition temperature of at least 121° C. and the third material preferably has a glass transition temperature of less than 121° C. It is also particularly preferred that the third material has a glass transition temperature of more than 50° C., in particular above 55° C., above 60° C., above 65° C., above 70° C., above 75° C. or above 80° C. It is also preferred that the first and the second material have a glass transition temperature of more than 125° C., in particular above 130° C., above 140° C., above 150° C., above 160° C., above 170° C. or above 180° C.

The glass transition temperatures of the first material and of the second material are preferably at least 5° C. higher, in particular at least 10° C. higher, at least 15° C. higher, at least 20° C. higher, at least 25° C. higher, at least 30° C. higher, at least 25° C. higher, at least 30° C. higher, at least 40° C. higher, at least 50° C. higher, at least 60° C. higher, at least 70° C. higher or at least 80° C. higher than the glass transition temperature of the third material.

One particularly preferred combination of materials is one in which the head plate and the container are made of polyamide, polycarbonate, polymethylpentene or polypropylene, and the stirring member and/or the mixer shaft is made of polystyrene. These materials have properties that render them suitable for use in both cell culture and also in microbiology. At the same time, the aforementioned materials for the head plate and the container differ in their temperature resistance from the aforementioned material for the stirring member and/or the mixer shaft in such a way that polyamide, polycarbonate, polymethylpentene or polypropylene withstand a decontamination process, in particular by steam sterilization, substantially unharmed, whereas steam sterilization causes the polystyrene to melt, with the consequence that the mixer shaft and the stirring member cannot be re-used.

Those aspects of the invention described so far may be applied singly or in any combination. More specifically, the developments of the invention as described in the following may be combined with single-use bioreactors according to any one of the aforementioned aspects or with any combination of said aspects.

One preferred embodiment is one in which the head plate and the container are bonded to each other. It is preferred, alternatively, that the head plate and the container are welded to each other, in particular by ultrasonic welding or by infrared welding. Joining the head plate and the container permanently by bonding or welding them together reduces the risk of contamination due to re-use or due to unintentional opening of the bioreactor. Ultrasonic welding, in particular, is preferred as a manufacturing technique, since it combines a high level of process reliability and the concomitantly reliable joining of the head plate and the container with fast and simple production involving reduced production cost and effort.

It is particularly preferred that the head plate is of integral construction. This reduces the number of parts in the reaction chamber, thus avoiding dead spots and gaps, and further also avoiding additional steps during assembly or construction of the single-use bioreactor. It is particularly preferred that the head plate is manufactured in an injection molding process.

The head plate is also made preferably of polyamide, polycarbonate, polymethylpentene or polypropylene. These materials have the advantage of meeting the requirements for use in both cell culture and in microbiology applications, while at the same time having a high temperature resistance.

Another preferred embodiment of the single-use bioreactor is one in which the head plate has a plurality of dip tubes on its inner side which project into the reaction chamber. These dip tubes are preferably in the form of hollow sleeves and can receive various instruments, sensors or conduits, in particular flexible tubes. The dip tubes are preferably rigid pipes. The dip tubes on the inner side of the head plate preferably match connectors on the outer side of the head plate, such that media or other items can be introduced into, or removed from the reaction chamber via the connectors and the dip tubes. The dip tubes, or at least some of them, preferably project so far into the reaction chamber that they dip into contents within the reaction chamber, for example a fluid, when the single-use bioreactor is used in the intended manner. Hence also the designation "dip tube". This has the advantage that no additional pipes or tubes need to be connected on the inner side of the head plate; the dip tubes already provided on the head plate, which are preferably integral with the entire head plate, can be used instead. This has the advantage that the production process can involve fewer assembly steps and also that the number of separate assemblies between which gaps or dead spots can ensue are reduced in the reaction chamber.

An embodiment of the single-use bioreactor is also preferred in which the head plate has a convex portion for receiving the bearing. Such an outwardly convex portion of the head plate is preferred in order to accommodate the bearing of the mixer shaft arranged in the reaction chamber and hence to reduce the usable reaction chamber space due to placement of the bearing only to a minimal extent. A rotary drive for the mixer may also be arranged on the convex portion on the outer side of the head plate. It is particularly preferred that the convex portion does not include an opening in the head plate, which is specifically preferred in the case of a magnetic coupling, in particular in the case of the aforementioned front-end magnetic coupling between the rotary drive and the mixer shaft.

It is particularly preferred that the bioreactor has a head plate as described further below or one of its developments. With regard to the special advantages, variants of the invention and details of the head plate and developments thereof, reference is made to the description provided below of the respective features of the head plate or one of its developments.

It is also preferred that the single-use bioreactor has a bearing housing which delineates a bearing chamber for accommodating the bearing inside the reaction chamber. The embodiment described here has the advantage, especially in combination with the aforementioned convexity in the head plate, that the bearing chamber is arranged partially, preferably predominantly, in the region of the convexity in the head plate and hence that a portion of the reaction chamber arranged below the head plate is substantially available for using the bioreactor in the intended manner. It is particularly preferred that the bearing housing delineates the bearing chamber from the reaction chamber, for example by means of a sliding bearing.

The bearing housing is preferably attached detachably to the inner side of the head plate or permanently joined to the inner side of the head plate. The bearing housing can be detachably attached by means of a snap-on, clip or screw connection, for example. The bearing housing can be permanently joined to the inner side of the head plate by bonding or welding, in particular by ultrasonic welding.

According to a fourth aspect of the invention, the objects initially specified are achieved by a biotechnological device comprising a single-use bioreactor of the kind described in the foregoing, according to any of its various aspects or developments, and a rotary drive having a magnetic drive portion which is arranged and adapted in such a way that it can be coupled magnetically in an axial direction to the magnetic portion of the mixer shaft.

The magnetic portion preferably consists of a composite material comprising a plastic matrix and a magnetic material, or includes such a composite material.

It is also preferred that the composite or two-component material that includes a magnet component is injection molded onto a front-face drive member of the rotary drive.

In one particularly preferred embodiment, the magnetic drive portion has a cross-section in a plane which is orthogonal to a rotational axis, and exerts a magnetic force over the major part of said cross-section, preferably over the entire cross-section, for a magnetic coupling in the axial direction to the magnetic portion of the mixer shaft.

Such a configuration of a preferably two-dimensional, contiguous cross-section of the region of the drive portion exerting a magnetic force may be achieved, more specifically, by injection molding a composite material comprising a plastic matrix and a magnetic material into an injection mold, which for its part contains a magnet for aligning the magnetic material of the composite during injection molding. The cross-section of the magnetic drive portion exerting a magnetic force is preferably circular, ellipsoidal or rectangular. Within this cross-section of the magnetic drive portion exerting a magnetic force, segments of differing polarity are preferably formed. For example, the segments may form a star-shaped pattern or a pattern with pie-shaped segments. The pattern formed by the segments of the magnetic drive portion preferably matches the pattern formed by the segments of the magnetic portion of the mixer shaft.

Such a configuration has several advantages. Firstly, a higher torque can be transmitted compared to an embodiment comprising a plurality of annularly arranged bar magnets. This is required, in particular, to achieve a higher rotor speeds in excess of 1500 rpm, in particular up to 2000 rpm, or up to 3000 rpm and more, speeds that are needed for applications in microbiology, in particular. It is possible at the same time to keep the required cross-sectional area of the rotary drive and hence the required construction space on the head plate small or low. By forming specific segment polarity patterns, it is possible to match bioreactors specifically to a correspondingly designed rotary drive and thus to increase the level of process reliability, since only bioreactors with matching segment polarities can be driven by a rotary drive. This is advantageous for ensuing that the drive has the desired torque and the desired speed, since torque and particularly the speed obtained are only monitored for mixers mechanically coupled to a rotational drive, however, not for magnetic coupling between mixer and rotational drive. A divergent speed can exert a negative influence on the cultivation process, for example when using a rotary drive with too low a power rating.

With regard to the advantages, variants of the invention and details of this biotechnological device and developments thereof, reference is made to the above description of the respective device features of the single-use bioreactor.

According to a fifth aspect of the invention, the objects mentioned at the outset are achieved by a head plate according to claim 10. Said head plate is particularly suitable for a single-use bioreactor of the kind described in the foregoing, and for the various aspects and developments thereof. The head plate comprises an inner side and an outer side opposite said inner side, the inner side having a plurality of dip tubes and the outer side having a plurality of connectors, and the head plate being of integral construction.

Such an integral configuration of a head plate, having a plurality of connectors on its outer side and simultaneously a plurality of dip tubes on its inner side, is advantageous in having a particularly high level of integration. This simplifies assembly of a single-use bioreactor significantly, in that the dip tubes replace conduits, such as tubes, that have to be mounted to connectors provided on the inner side of prior art head plates. By virtue of this integral construction, the number of parts in the reaction chamber and thus the number of gaps and dead spots is reduced.

It is particularly preferred that the dip tubes are of such a length that the dip tubes dip into the contents or the culture broth when a single-use bioreactor with which the head plate is used is filled to a minimum filling volume. It is preferred, more specifically, that the length of the dip tubes is at least 85 per cent of a diameter of the head plate. Diameter is understood here to be the diameter of a head plate of circular cross-section, for example. In the case of a head plate having an elliptical or rectangular cross-section, diameter is understood to be an extension of the head plate in one of its two main directions of extension.

It is particularly preferred that the length of the dip tubes is more than 50 per cent, preferably at least 75 per cent, at least 80 per cent, at least 85 per cent, at least 90 per cent or at least 95 per cent of the diameter of the head plate. It is also preferred that the length of the dip tubes is at least equal to the diameter of the head plate. A preferred length of the dip tubes is one that is more than 1.1 times, more than 1.2 times, more than 1.3 times, more than 1.4 times, more than 1.5 times, more than 1.6 times, more than 1.7 times, more than 1.8 times, more than 1.9 times or more than 2 times the diameter of the head plate.

The head plate preferably has at least three, or more specifically at least five dip tubes.

The dip tubes preferably have an inner diameter that is less than 8 millimeters, in particular less than 7 millimeters, less than 6 millimeters, less than 5 millimeters, less than 4.8 millimeters, less than 4.75 millimeters, less than 4.7 millimeters, less than 4.5 millimeters, less than 4.3 millimeters, less than 4 millimeters, less than 3.5 millimeters, less than 3 millimeters, less than 2.5 millimeters, less than 2 millimeters, less than 1.5 millimeters or less than 1 millimeter.

It is also preferred that at least two, preferably several of the dip tubes of a head plate have different inner diameters. It is further preferred that at least two, preferably several of the dip tubes of a head plate have different lengths. These embodiments are preferred in order to adapt the dip tubes to different applications, so that a single-use bioreactor having such a head plate can be used in a wide and flexible range of applications.

It is particularly preferred that the head plate is manufactured in an injection molding process.

The head plate is preferably made of polyamide, polycarbonate, polymethylpentene or polypropylene. These materials have the advantage of meeting the requirements for use in both cell culture and in microbiology applications, while at the same time having a high temperature resistance.

In addition, the head plate preferably has a convex portion for receiving a bearing of a mixer. This is preferred, in particular, when the head plate is meant to be used as the head plate of a single-use bioreactor, as described in the foregoing, having a magnetic coupling between the mixer and the rotary drive.

It is particularly preferred that the diameter of at least one of the dip tubes tapers at the end which faces away from the head plate. This tapering dip tube and/or one or more of the other dip tubes is preferably closed at the end facing away from the head plate, and is also preferably provided at said closed end with an orifice, said orifice preferably having a diameter that is less than the inner diameter of the dip tube. This is specifically preferred when such a dip tube is be deployed as a gassing tube.

The dip tubes preferably have a wall thickness of less than 3 millimeters, in particular a wall thickness of less than 2 millimeters, less than 1.5 millimeters or less than 1 millimeter.

At least one, and preferably two of the connectors on the outer side of the head plate has/have a thread, preferably an internal thread. In this way, it is possible to provide screw connections on the connectors, without additional connector members having to be mounted for this purpose on the head plate.

According to a sixth aspect of the invention, the object specified at the outset is achieved by a process for manufacturing a single-use bioreactor according to claim 12. According to a seventh aspect of the invention, or according to one development of the preceding aspect, the aforementioned object is achieved by a process for manufacturing a single-use bioreactor according to claim 13. According to an eighth aspect of the invention, the aforementioned object is achieved by a process for manufacturing a head plate for a single-use bioreactor according to claim 14. With regard to the advantages, variants of the invention and details of these aspects of the inventive manufacturing process, and developments thereof, reference is made to the preceding description regarding the respective product features of the single-use bioreactor and the head plate.

DESCRIPTION OF PREFERRED
EMBODIMENTS OF THE INVENTION

Figure 1B:
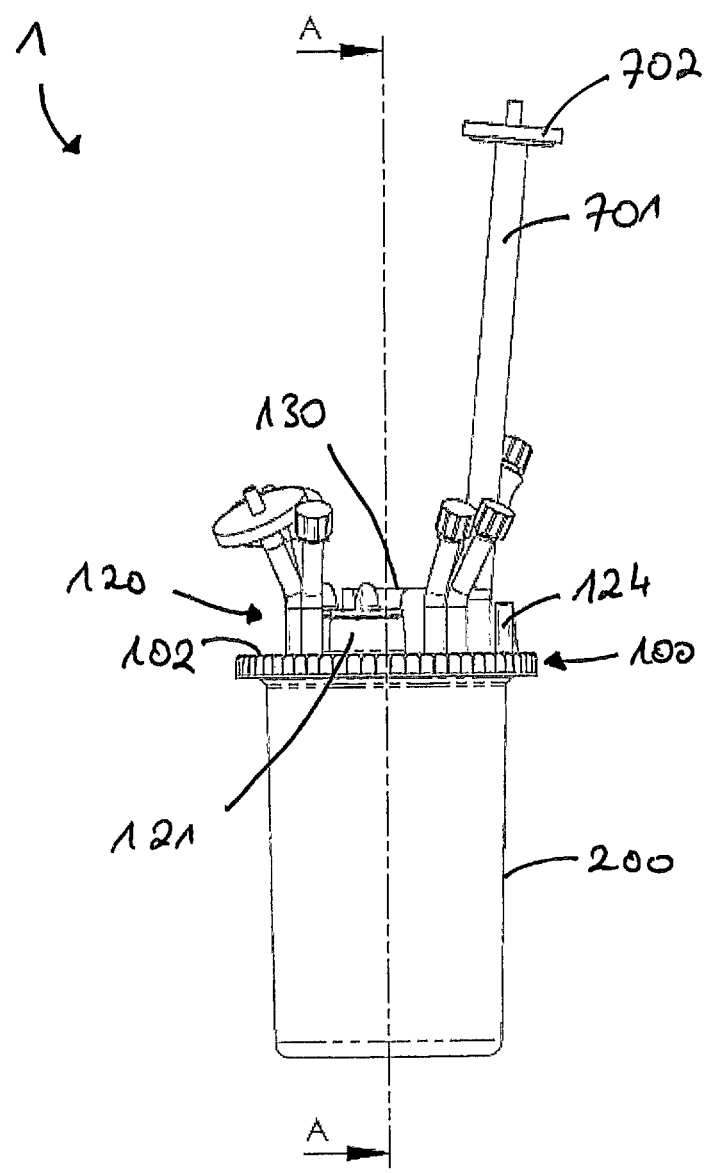
Figure 1C:
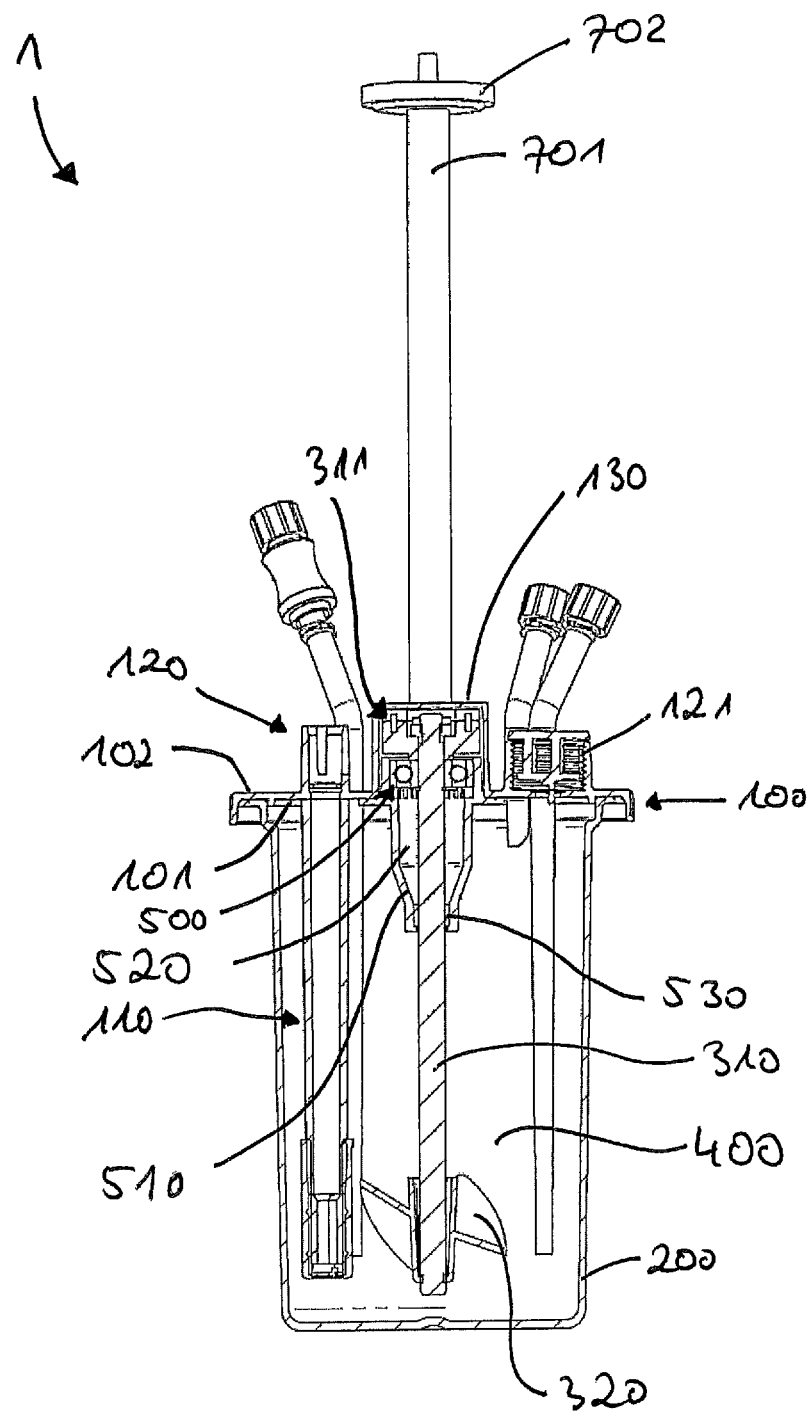
Figure 1D:
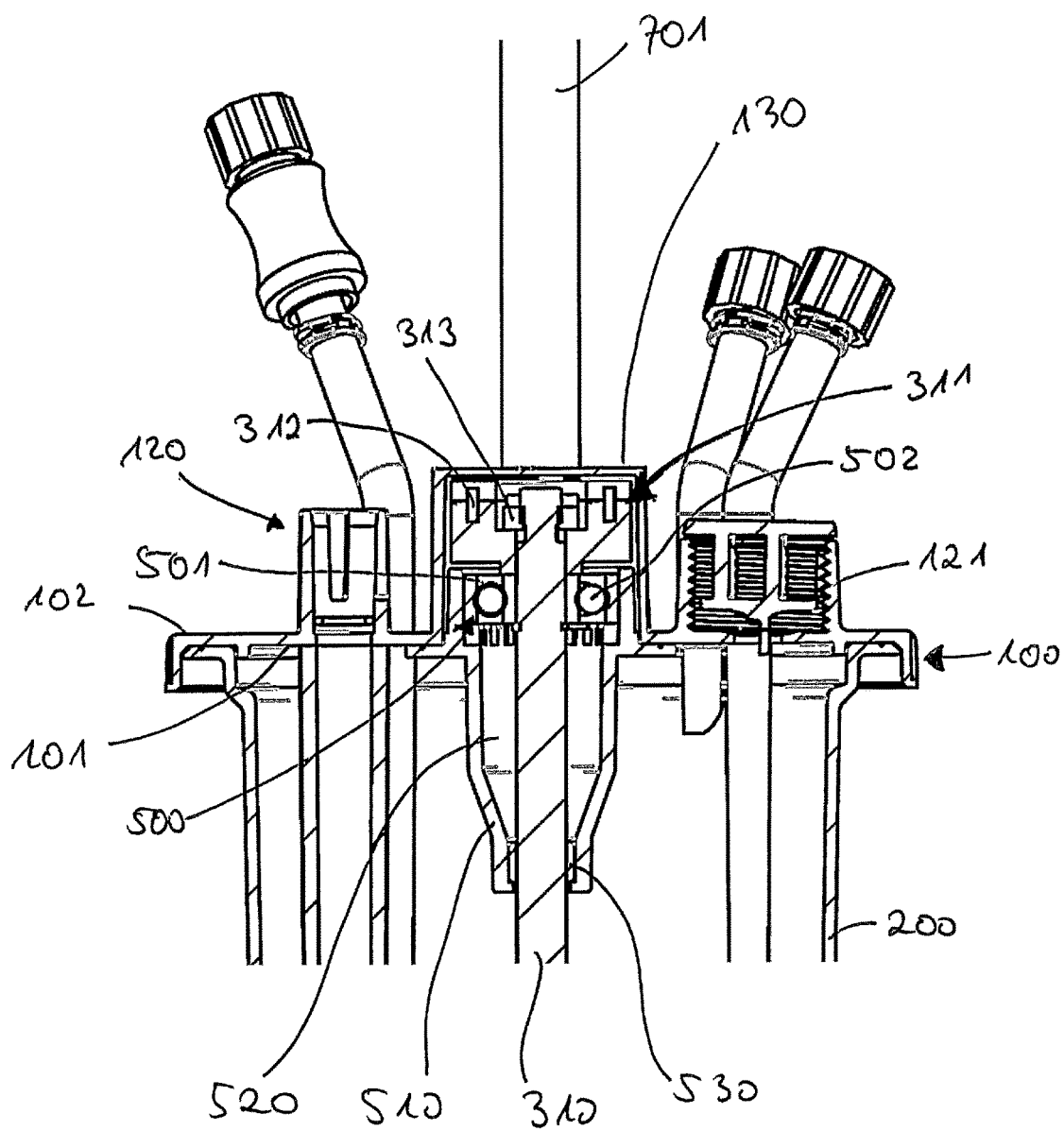
Figure 1E:
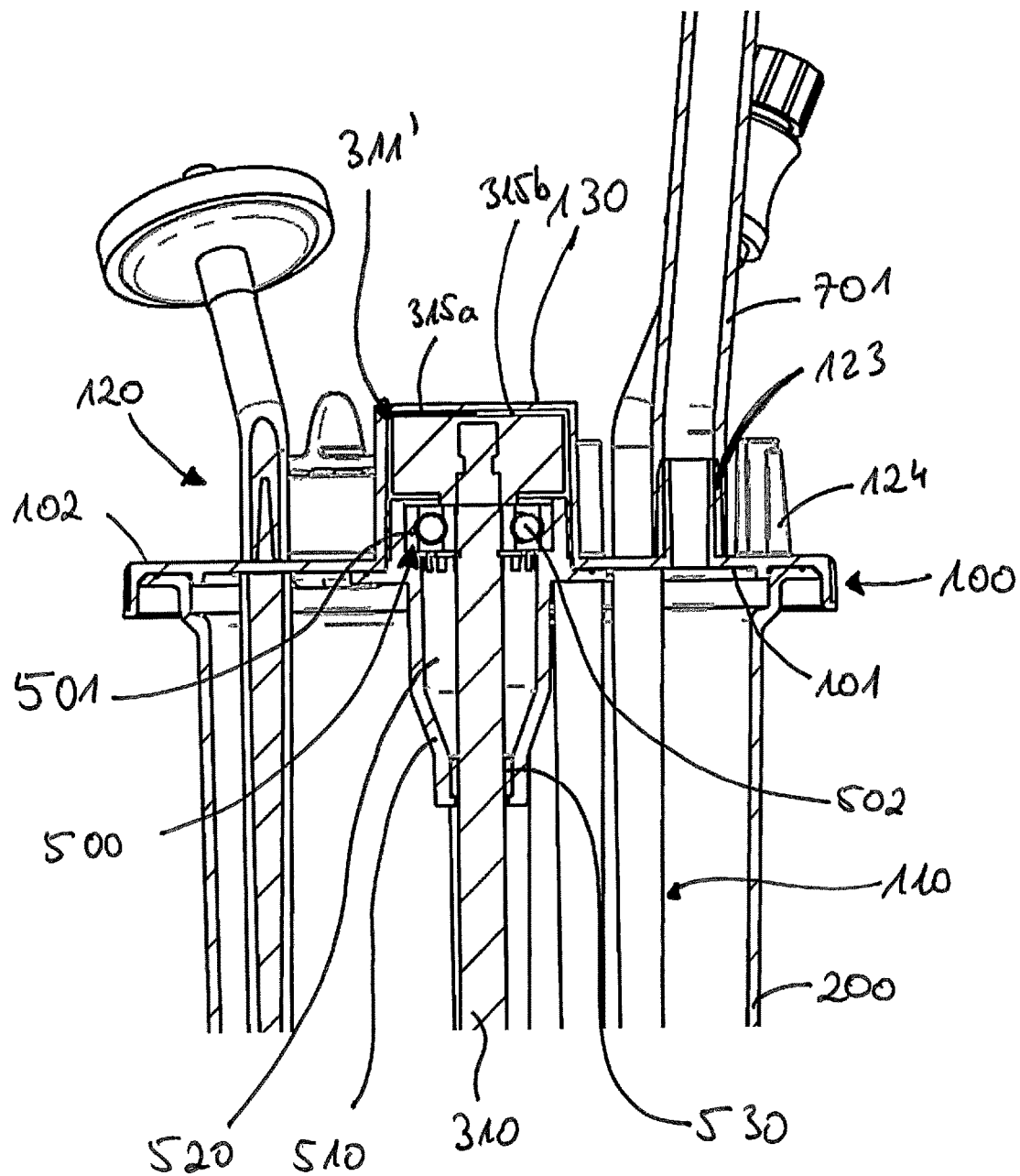
Figure 2A:
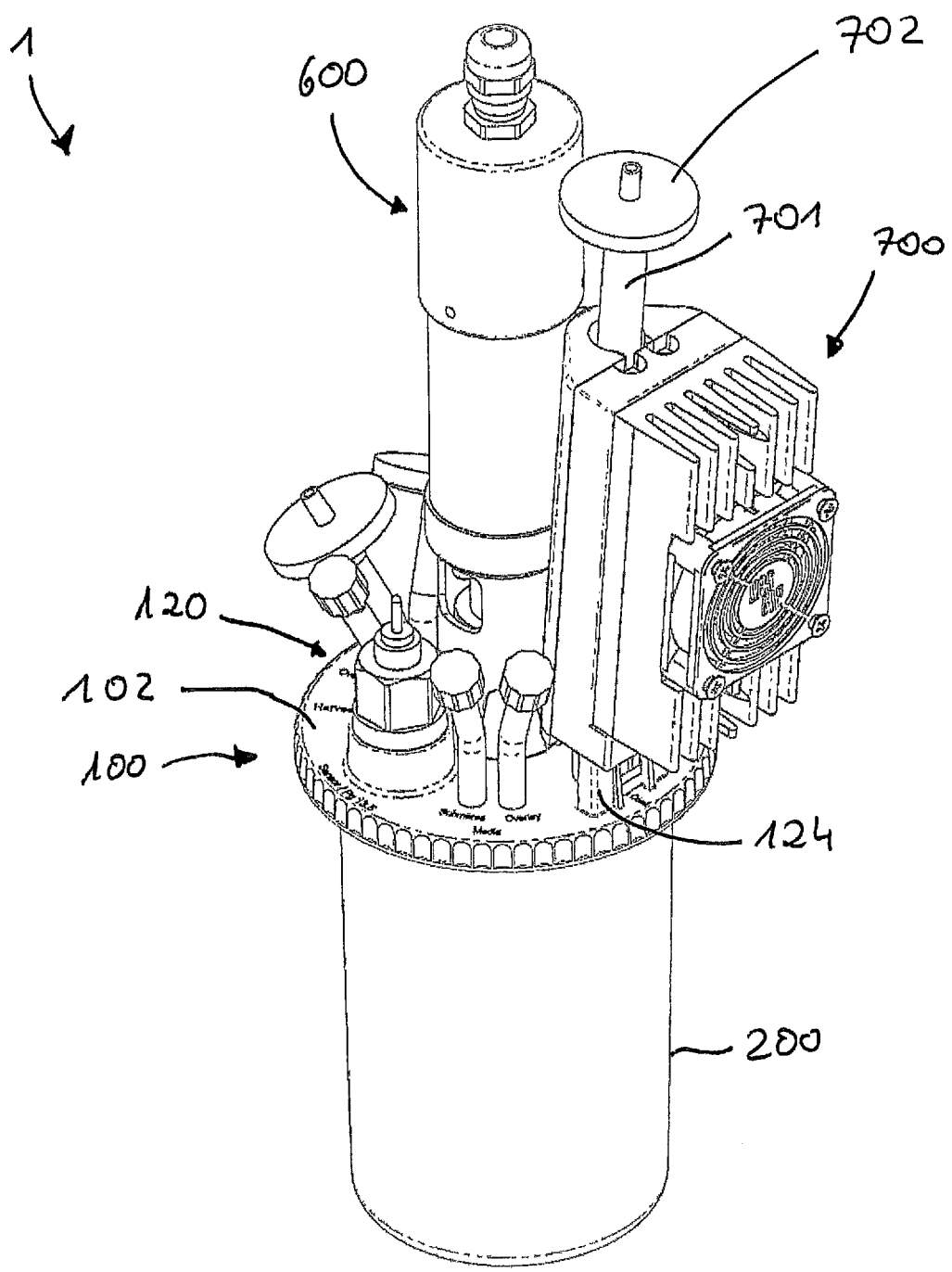
Figure 2B:
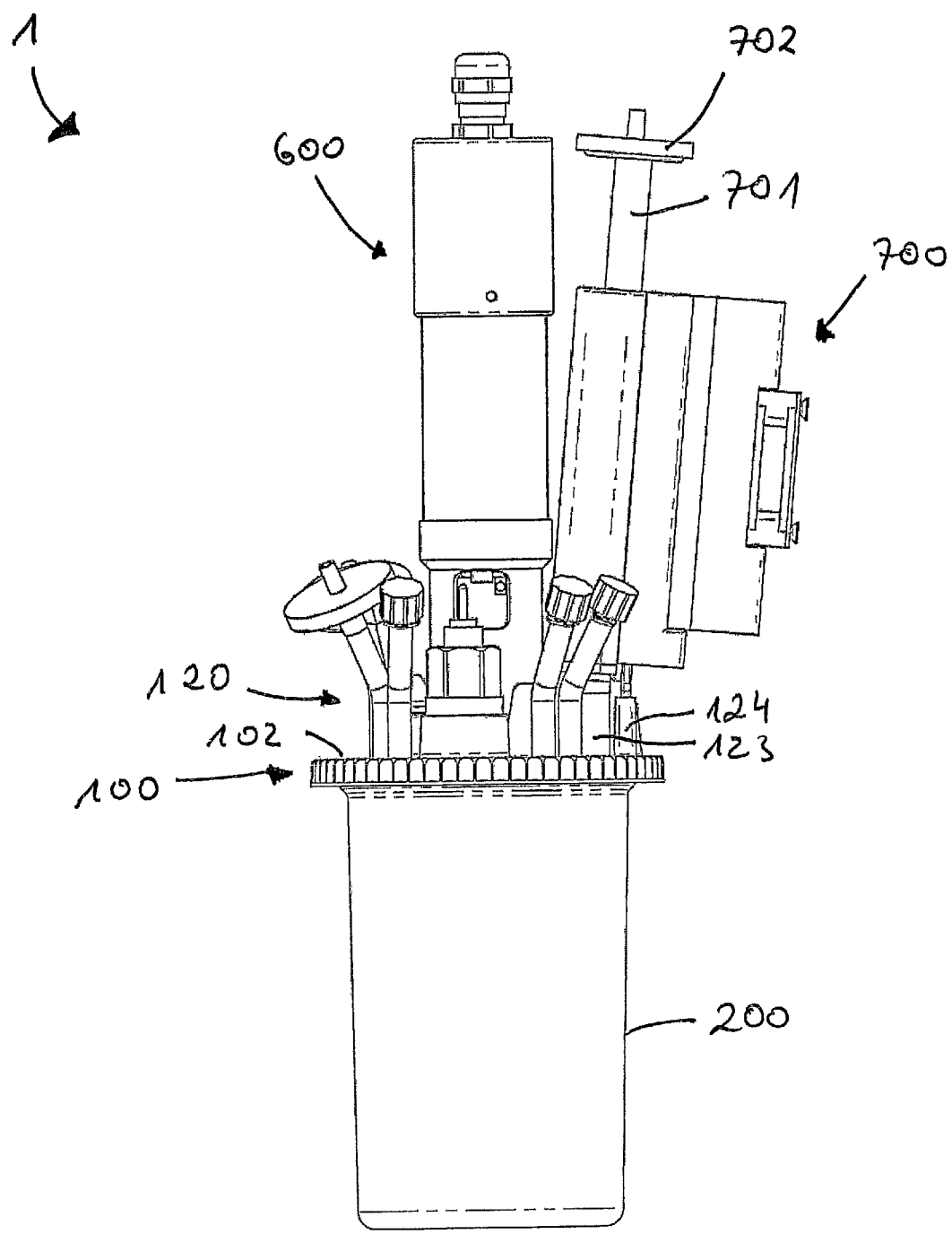
Figure 2C:
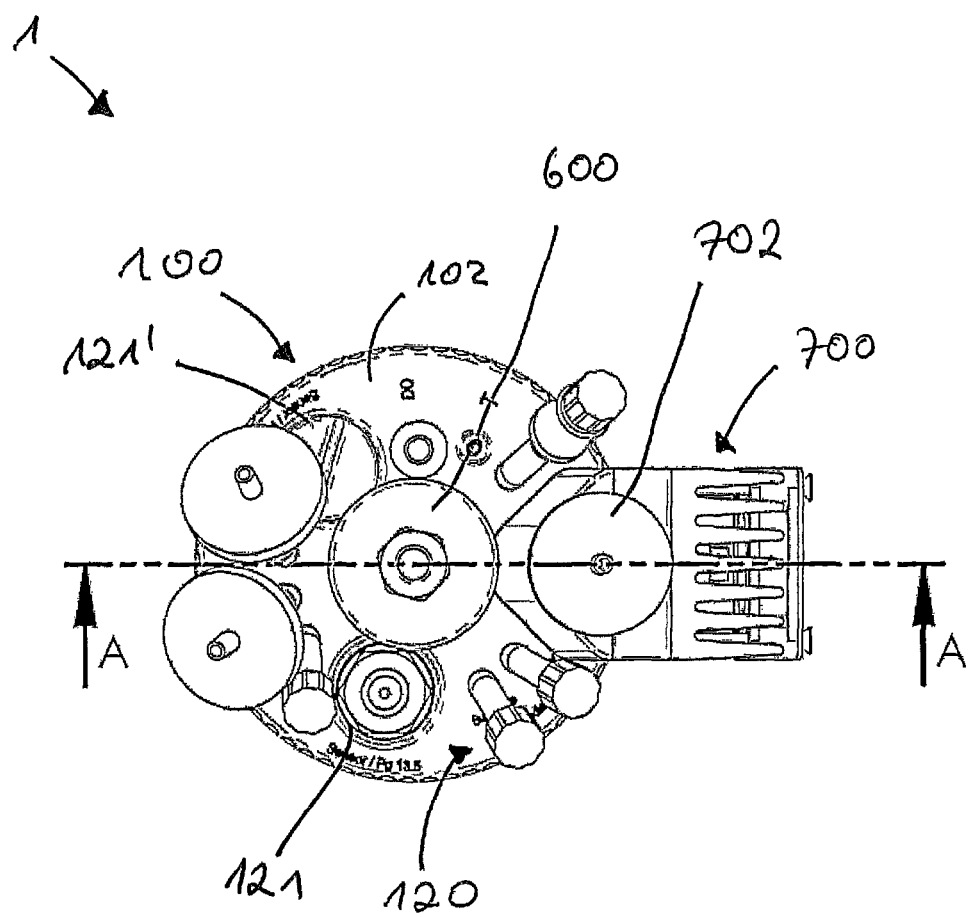
Figure 2D:
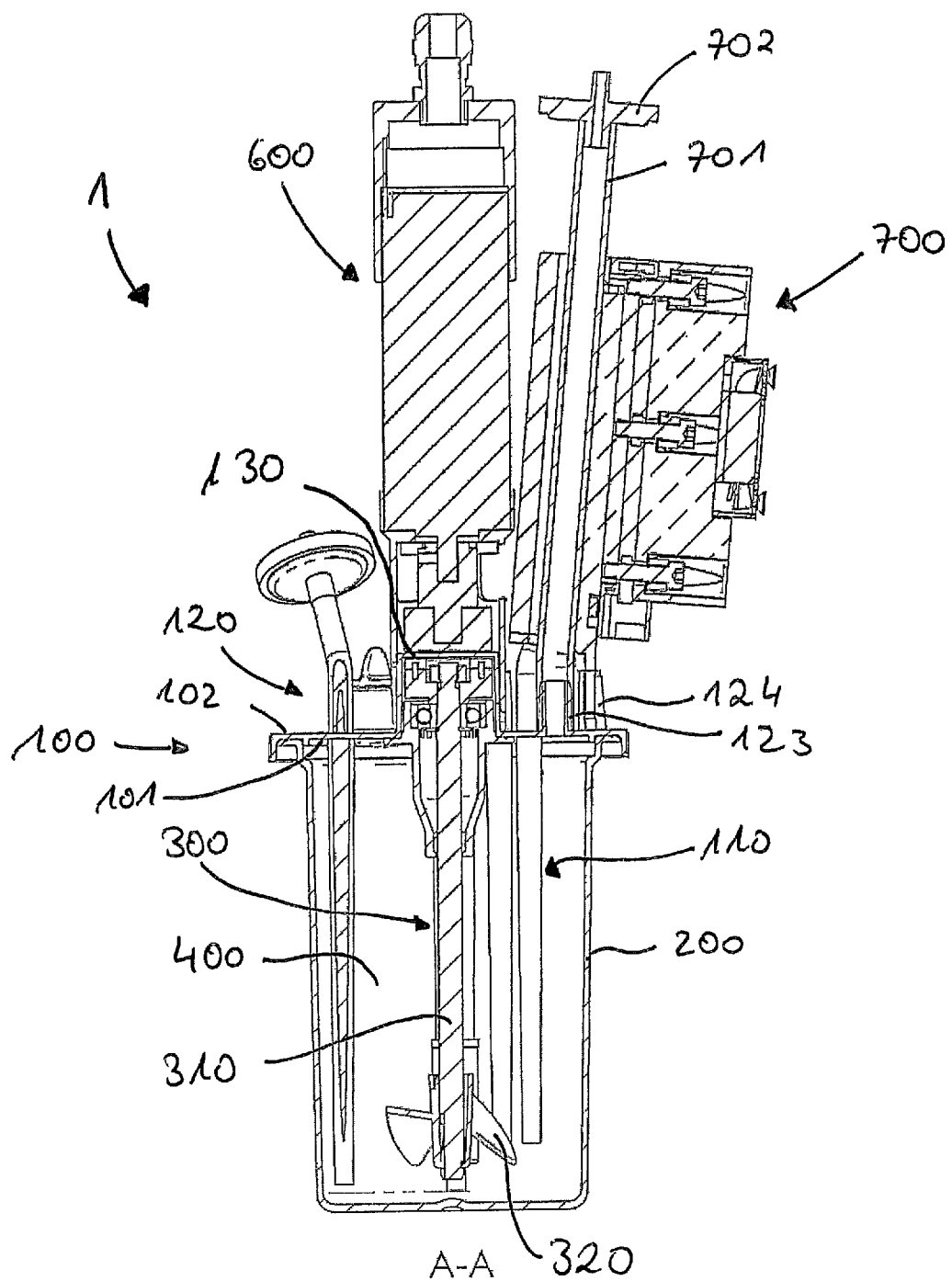
Figure 2E:
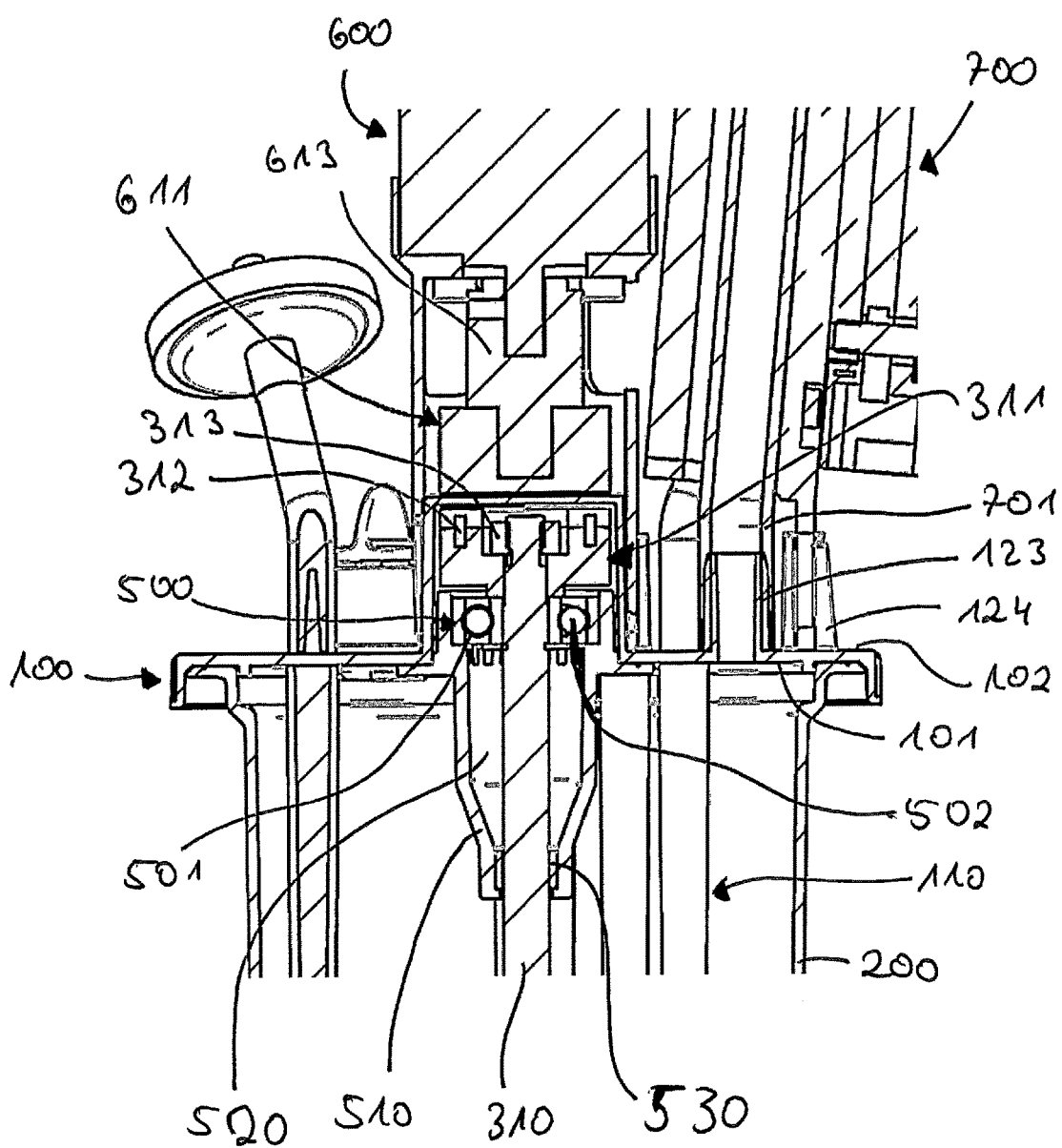
Figure 2F:
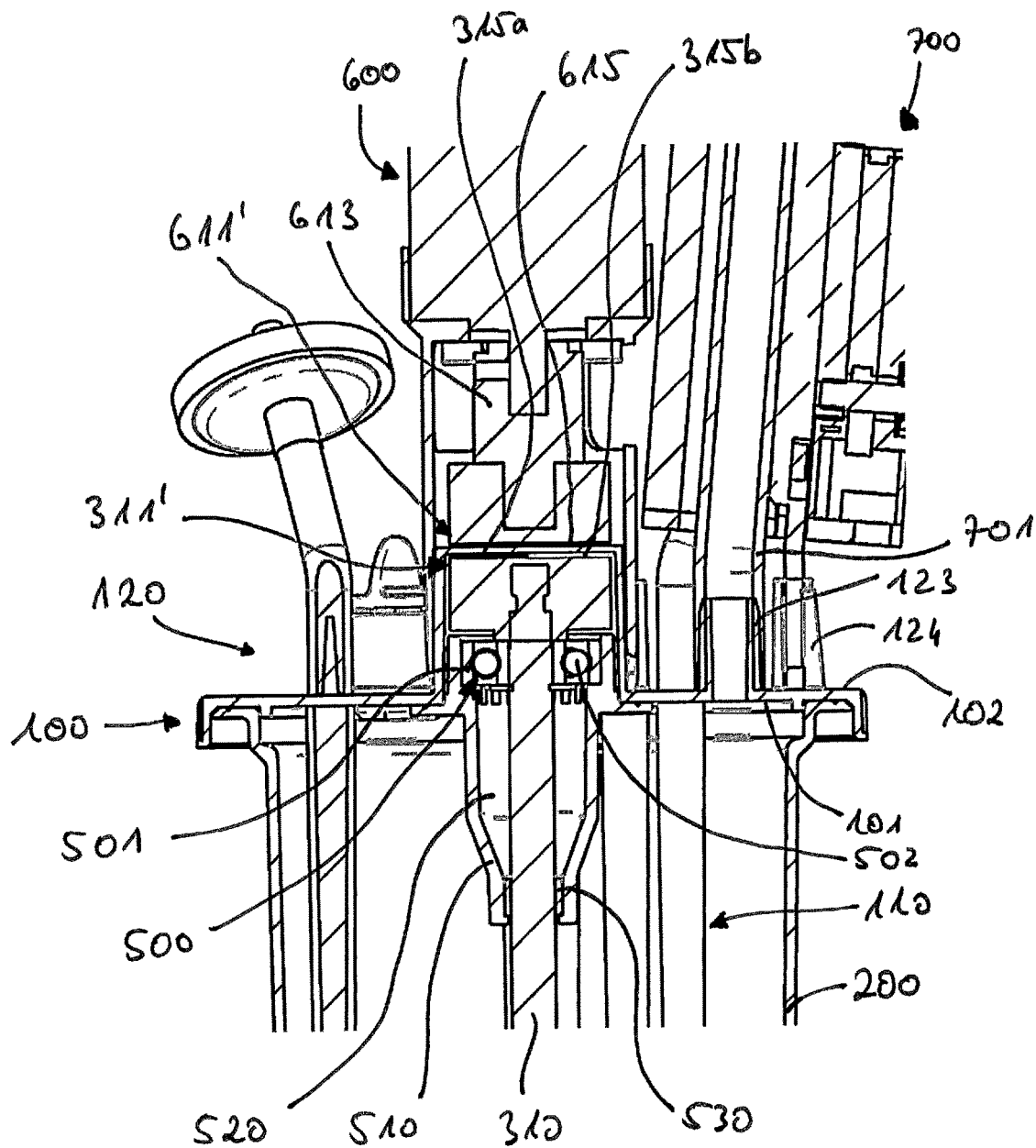
Figure 3:
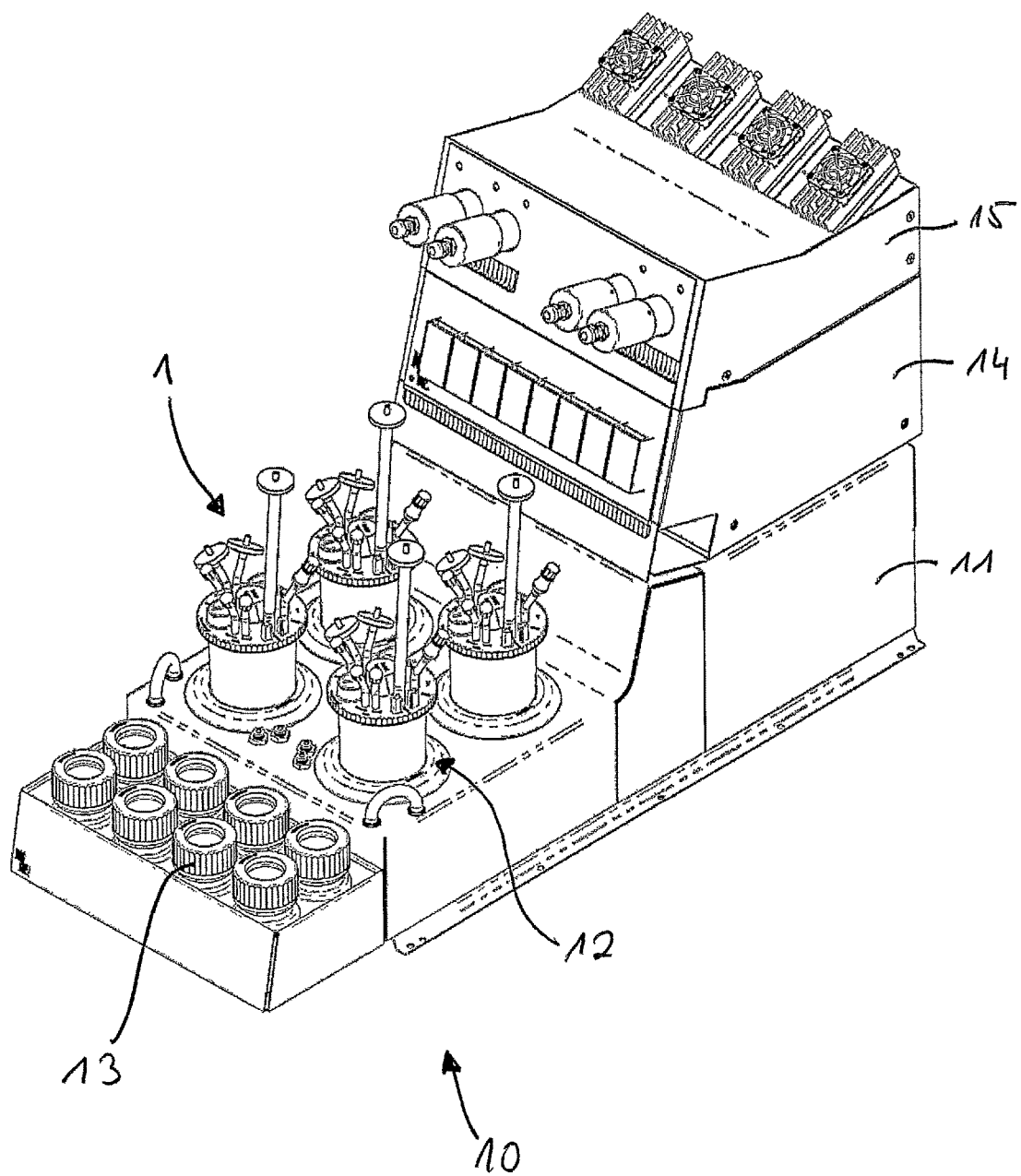
Figure 4A:
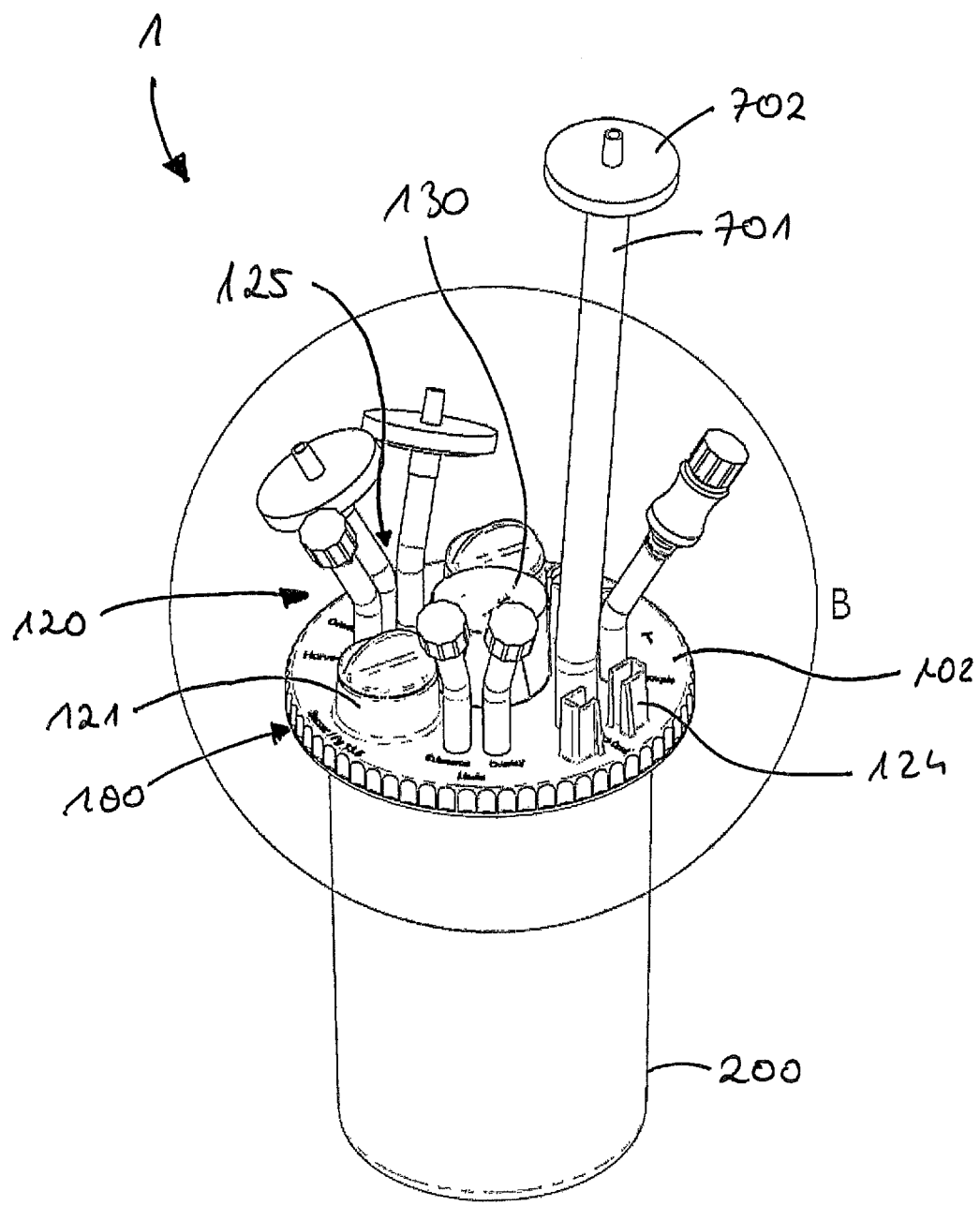
Figure 5A:
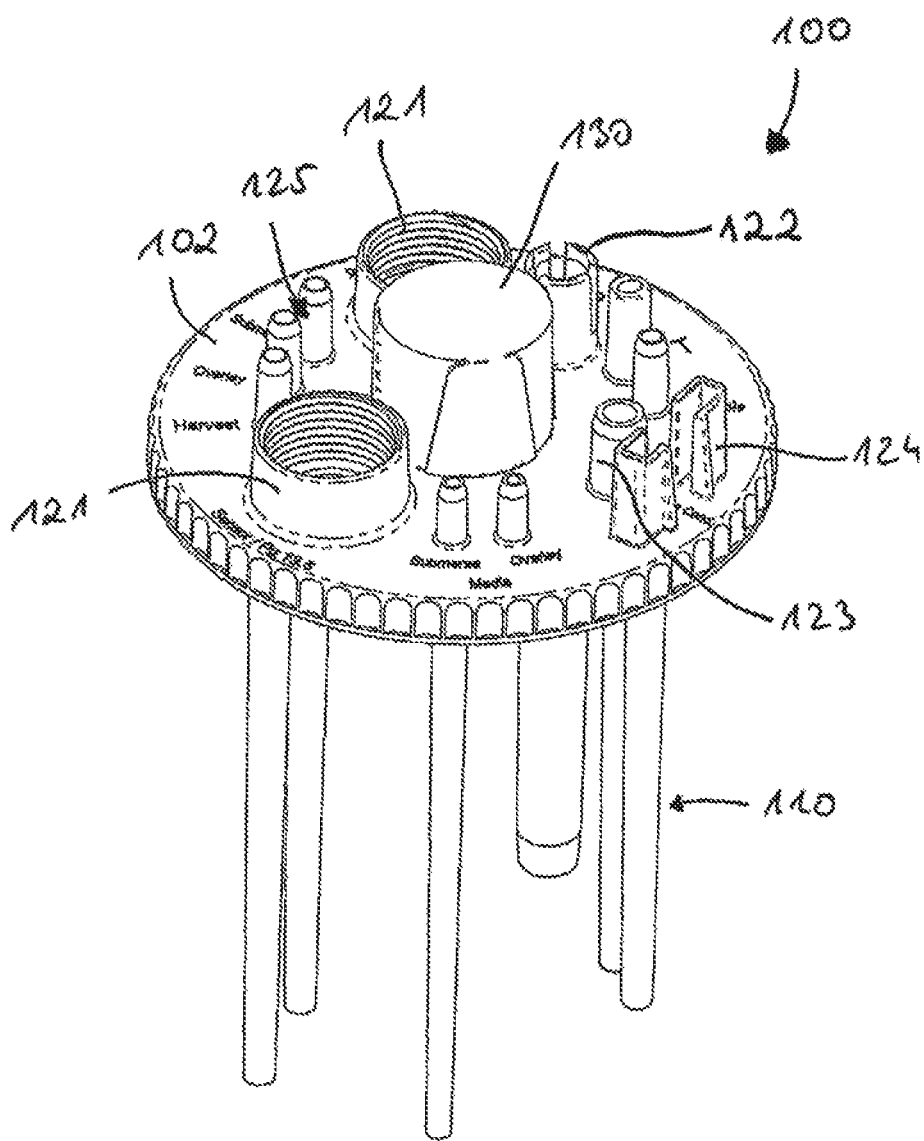
Figure 5B:
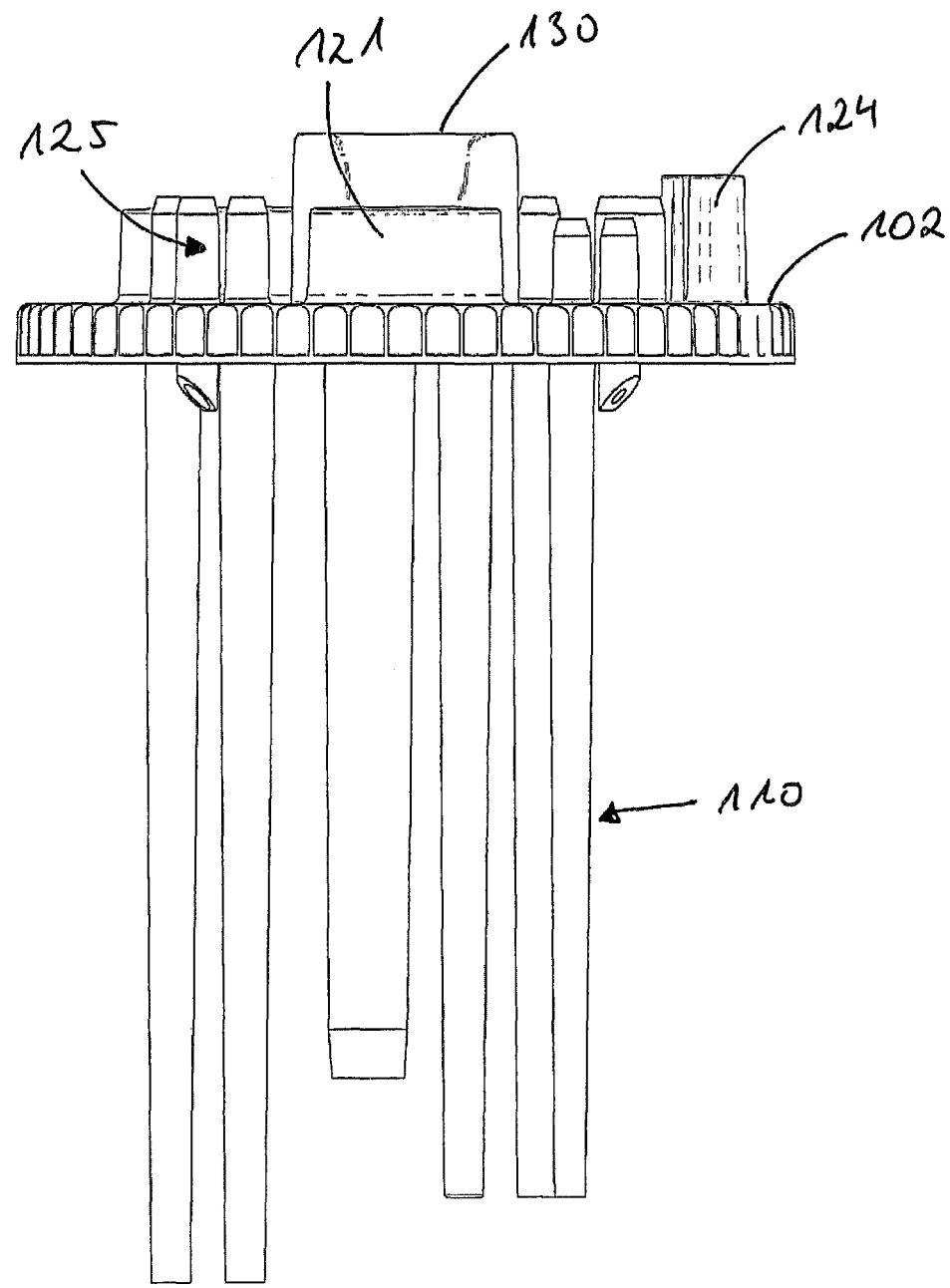

Some possible embodiments of the invention shall now be described by way of example with reference to the attached Figures, in which:

FIG. 1A: shows a three-dimensional view of an embodiment of a single-use bioreactor according to the invention;

FIG. 1B: shows a side view of the single-use bioreactor in FIG. 1A;

FIG. 1C: shows a cross-section of the single-use bioreactor in FIG. 1A along the sectional plane A-A in FIG. 1C;

FIG. 1D: shows an enlarged section from FIG. 1C;

FIG. 1E: an alternative embodiment of the magnetic portion;

FIG. 2A: shows a three-dimensional view of a biotechnological device comprising a single-use bioreactor, a connection device and a temperature control device;

FIG. 2B: shows a side view of the biotechnological device in FIG. 2A;

FIG. 2C: shows a plan view of the biotechnological device in FIG. 2A;

FIG. 2D: shows a cross-section of the biotechnological device in FIG. 2A along the sectional plane A-A in FIG. 2C;

FIG. 2E: shows an enlarged section from FIG. 2D;

FIG. 2F: an alternative embodiment of the magnetic portion of the mixer shaft and of the magnetic drive portion of the rotary drive;

FIG. 3: shows a parallel bioreactor system;

FIG. 4A: shows the single-use bioreactor in FIG. 1A, indicating a section B for enlargement;

FIG. 4A: shows the enlarged section B from FIG. 4A;

FIG. 5A: shows a three-dimensional view of a head plate;

FIG. 5B: shows a side view of the head plate in FIG. 5A; and

Figure 5C:
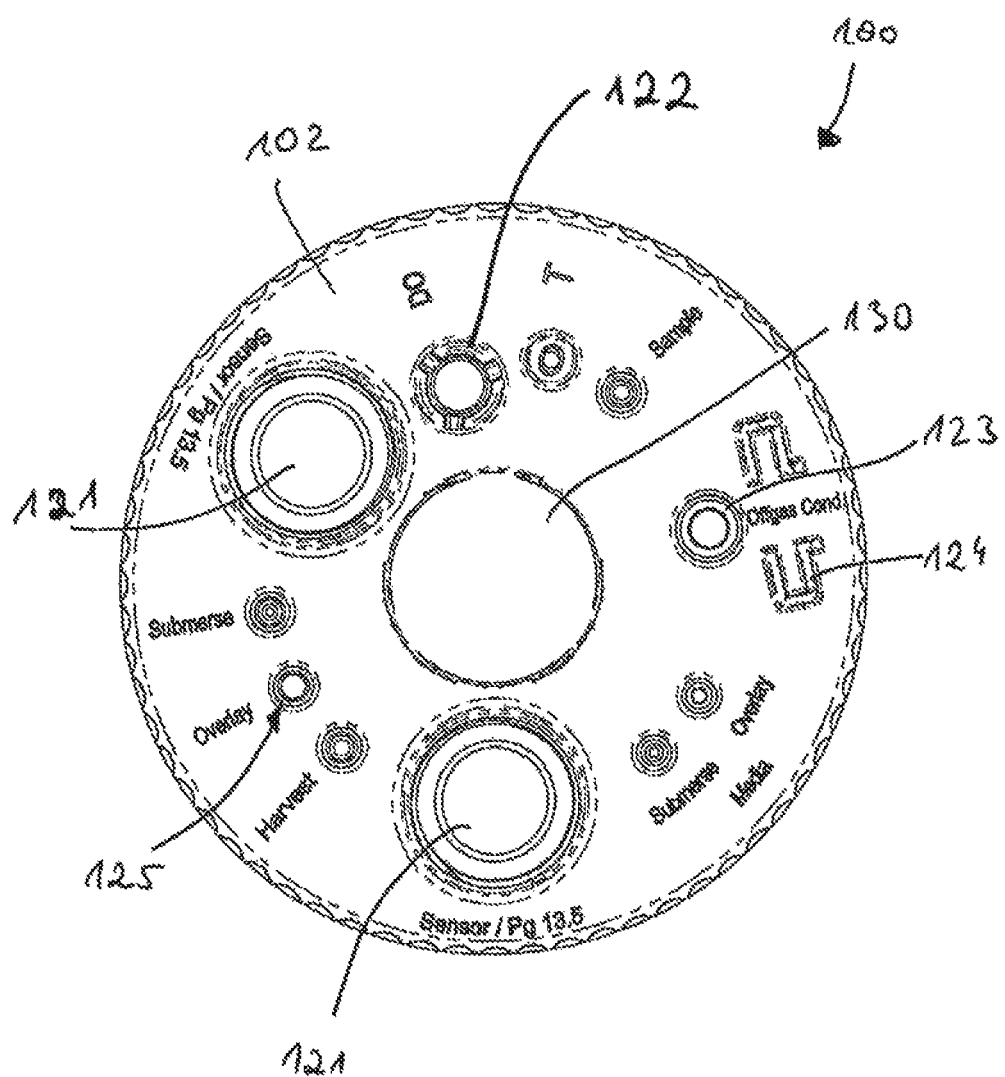

FIG. 5C: shows a plan view of the head plate in FIG. 5A.

FIGS. 1 to 5 show, by way of example, certain embodiments of the invention and how it is applied. Identical or similar elements are marked in the Figures with the same reference signs.

FIGS. 1A, 1B, 1C, 1D, 1E and FIGS. 2A, 2B, 2C, 2D, 2E, 2F show a single-use bioreactor 1 and a biotechnological device comprising a single-used bioreactor, a connection device and a temperature control device for use in a parallel bioreactor system 10, as shown in FIG. 3, for applications in cell culture and/or in microbiology. The parallel bioreactor system 10 shown in FIG. 3 has a base block 11 with four receptacles 12 arranged therein, into each of which a bioreactor 1 can be detachably inserted. A temperature control unit configured to heat or cool the bioreactors 1 arranged in receptacles 12, as required, is preferably arranged in base block 11. An arrangement with containers 13 is formed adjacent to base block 11. Base block 11 also includes a stacking surface on which two functional blocks 14, 15 are removably arranged in a stack, the latter being configured, for example, as a deposit and display station or a pump station, for example to supply or remove the fluid necessary for operating the bioreactors. Such a parallel bioreactor system 10 has the advantage of having a small footprint and a high degree of scalability, since a plurality of these parallel bioreactor systems 10 each having four single-use bioreactors 1 can be arranged side by side. The single-use bioreactors 1 have the advantage that they can be used like reusable bioreactors in such a parallel bioreactor system for applications in cell culture and/or microbiology.

Single-use bioreactor 1 has a head plate 100, a dimensionally stable container 200 and a mixer 300. Head plate 100 and container 200 enclose a reaction chamber 400. Head plate 100 has an inner side 101 facing towards the reaction chamber, on which inner side a plurality of dip tubes 110 which project into reaction chamber 400 are arranged. A plurality of connectors 120 are arranged on an outer side 102 of head plate 100 facing towards reaction chamber 400.

Mixer 300 has a mixer shaft 310 with an axis of rotation and a stirring member 320. Stirring member 320 is embodied here with vanes pitched at 45°, for example as a pitched-blade impeller. As an alternative, at least one Rushton impeller may also be used as the stirring member. Stirring member 320 is attached torsionally rigidly to mixer shaft 310, with the result that rotation of mixer shaft 310 causes stirring member 320 to rotate as well.

Head plate 100 and container 200 are preferably made of polyamide and permanently joined to each other by ultrasonic welding. Mixer 300, in particular mixer shaft 310 and/or stirring member 320, are preferably made of polystyrene. Polystyrene has a lower temperature resistance than polyamide, so when single-use bioreactor 1 is subjected to steam sterilization, mixer 300 is rendered unusable, thus excluding any re-use of the single-use bioreactor 1.

Mixer shaft 310 is mounted rotatably about a rotational axis in a bearing 500. Bearing 500 is arranged in a convex portion 130 of head plate 100. A bearing housing 510 encloses a bearing chamber 520 in reaction chamber 400. Mixer shaft 310 is passed through bearing housing 510 via a sliding bearing 530. The entire bearing housing may preferably consist of a material which is suitable for a sliding bearing. This has the advantage of reducing the number of single parts and of achieving a high level of integration, which also has advantageous implications for manufacture and assembly. Bearing 500 is designed as a roller bearing and preferably is a polymer roller bearing 501 with a polyethylene, polypropylene, polyvinylidene fluoride, polyether ether ketone or polytetrafluoroethylene ball race and glass ball bearings 502.

Mixer 300 and bearing 500 are completely arranged in the reaction chamber 400. As can be seen from FIGS. 1D, 1E and 2E, 2F, mixer shaft 310 has a magnetic portion 311 which is coupled magnetically in an axial direction to rotary drive 600. Magnetic portion 311, 311' of mixer shaft 310 is magnetically coupled to a rotary drive 600 at the front face, i.e. in the axial direction. Rotary drive 600 is substantially cylindrical and has a cross-sectional area which is substantially identical to the cross-sectional area of convex portion 130 on head plate 100. A drive member 613 drives a magnetic drive portion 611, 611'. The front-face axial magnetic coupling shown in FIGS. 1D, 1E and 2E, 2F exhibits the advantage of the drive unit of the head plate requiring particularly little space.

In the embodiment shown in FIGS. 1D and 2E, a magnetic portion 311, in which magnets 312 are preferably arranged in an annular arrangement, is arranged at the end of mixer shaft 310. In the embodiment shown in FIGS. 1D and 2E, magnetic portion 311 with magnets 312 arranged therein is connected torsionally rigidly via a hexagon nut 313 to mixer shaft 310. Magnets may be arranged also in the magnetic drive portion 611 of the rotary drive 600, which are preferably aligned with the arrangement of the magnets 312 of the magnetic portion 311 of mixer shaft 310.

In an alternative, particularly preferred embodiment shown in FIGS. 1E and 2F, the magnetic portion 311' has a cross-section in a plane which is orthogonal to the mixer shaft 310, and exerts a magnetic force over the major part of said cross-section, preferably over the entire cross-section, for a magnetic coupling to a rotary drive 600 in the axial direction. The cross-section of the magnetic portion 311' exerting a magnetic force is preferably circular in shape here, and preferably has segments 315a,b of differing polarity that form, for example, a star-shaped pattern or a pattern with pie-shaped segments.

Preferably, also the magnetic drive portion 611' of the rotational drive 600 has a cross-section in a plane which is orthogonal to a rotation axis, and exerts a magnetic force over the major part of said cross-section, preferably over the entire cross-section, for a magnetic coupling to a magnetic portion 311' of mixer shaft 310 in the axial direction.

The cross-section of the magnetic drive portion 611' exerting a magnetic force is preferably circular in shape here, and preferably has segments 615 of differing polarity that form, for example, a star-shaped pattern or a pattern with pie-shaped segments. The pattern formed by the segments 615 of the magnetic drive portion 611' preferably matches the pattern formed by the segments 315a,b of the magnetic portion 311' of the mixer shaft 310.

The magnetic portion 311' and/or the magnetic drive portion 611' are preferably made of a composite or two-component material, in particular a magnet/polymer mixture, and further preferably made in an injection molding process. The magnetic portion 311' and/or the magnetic drive portion 611' may be separate parts, which are arranged at the mixer shaft 310 or drive member 613 and, preferably detachably, attached thereto.

Particularly preferred is that magnetic portion 311' is integral with mixer shaft 310, preferably by injection molding a composite or two-component material in particular a magnet/polymer mixture, onto an end of mixer shaft 310. Further, it is particularly preferred that magnetic drive portion 611' is integral with drive member 613, preferably by injection molding a composite or two-component material in particular a magnet/polymer mixture, onto drive member 613.

The head plate 100 shown in FIGS. 5A, 5B, 5C, specifically, is preferably of integral construction and preferably made of polyamide in an injection molding process, including the connectors 120 arranged on its outer side and the dip tubes 110 arranged on its inner side. Dip tubes 110 match a part of connectors 120, such that instruments, sensors, conduits or tubes can be inserted into and removed from the reaction chamber through corresponding connectors 120 and through dip tubes 110. Connectors 120 are used to provide the substances necessary for the reaction process and/or to remove substances, such as gases produced during operation, from reaction chamber 400. Connectors 120 can also be referred to as the overlay, and dip tubes 110 as submersibles.

Connector 123, for example, is used for connecting to an exhaust gas tube 701, at the end of which a sterile exhaust gas filter 702 is arranged. An exhaust gas stream discharged through exhaust gas tube 701 can be treated, for example, by another device, preferably a temperature control device. Sterile filter 702 is used to filter the exhaust gas before it is discharged. Next to connector 123 for an exhaust gas tube 701, a connection slot 124 is formed by two U-shaped profiles that are suitable, in particular, for receiving an exhaust gas cooling element 700. Exhaust gas cooling element 700 may be embodied as a cooling element, as described in the applicant's parallel application of the same day bearing the title "Device for a sterile single-use fluid conduit of a single-use bioreactor and methods for treating a fluid stream". Such a cooling element 700 is used to cool the exhaust gas in tube 701 and to condense any fluid which is transported therein, which can then be returned to reaction chamber 400, preferably by the force of gravity, so that it is available again in the reaction chamber and does not clog the sterile filter 702.

Figure 4B:
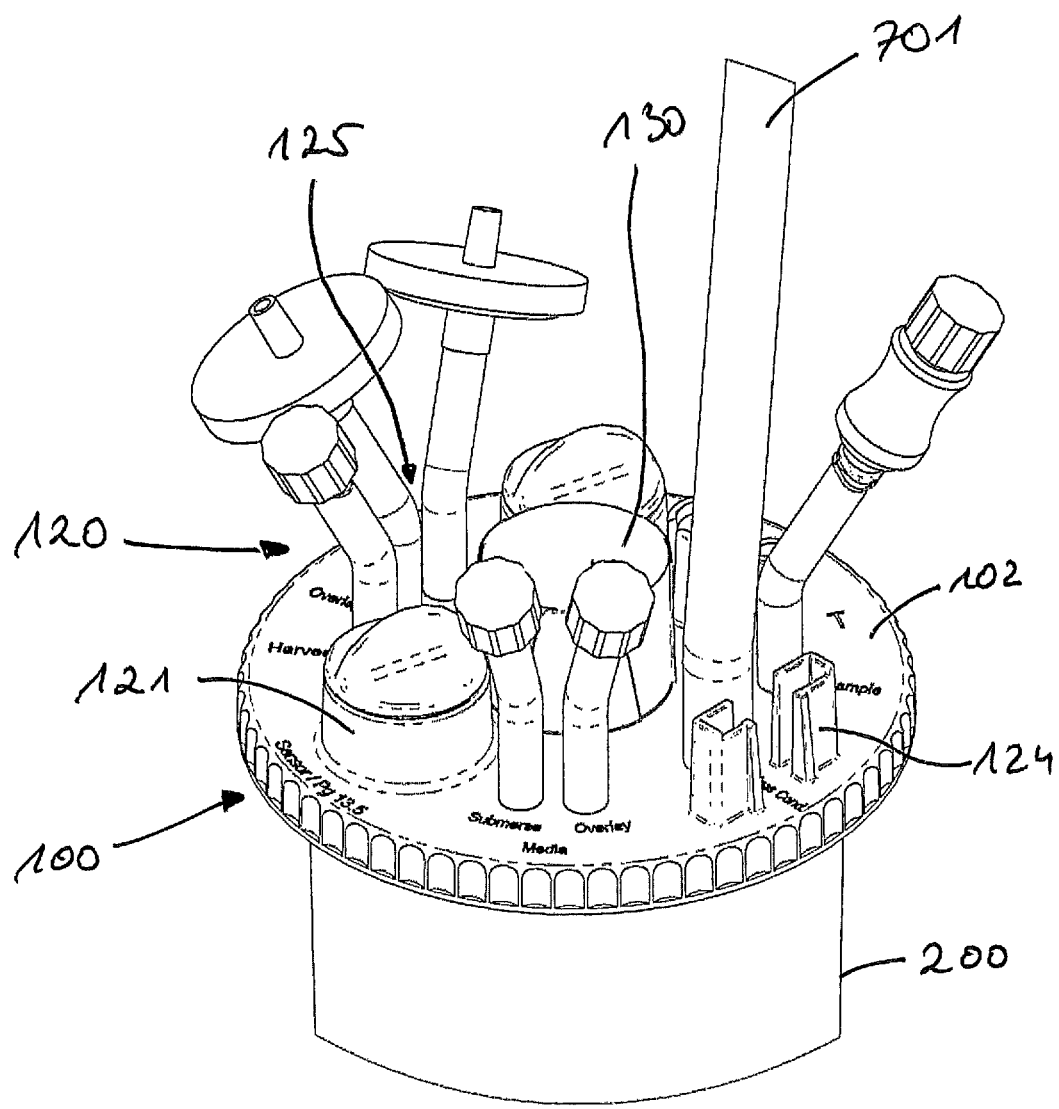

Connectors 120 may be embodied as screw connectors 121 with an internal thread, for example, or as clamp connectors 122 or as cone-shaped connectors 125. The arrangement of connectors 120 and dip tubes 110 shown in FIGS. 5A, 5B, 5C provides a high level of flexibility, so a single-use reactor with such a head plate 100 is suitable for many applications not only in the field of cell culture, but also in microbiology. Connectors 120 which are not needed can be closed for the application, as shown, for example, for the two screw connectors 121 in FIGS. 1A and FIGS. 4A, 4B. Three conical connectors 125 arranged between the two screw connectors 121 can be seen in FIGS. 5A, 5B, 5C, for example, and FIGS. 4A, 4B show them with tubes pushed onto them. In the variant shown in FIG. 2C, the rear one of the two screw connectors 121 is closed by a cap, whereas the front one of the two screw connectors 121 supports a functional element. Sensors for detecting pH, dissolved oxygen (DO) or temperature, for example, or other kinds of sensors may be connected to connectors 120 and preferably inserted into the reaction chamber via dip tubes 110. The two screw connectors 121 are preferably embodied as Pg 13.5 ports.

One particularly preferred combination of connectors 120 and a head plate 100 contains two screw connectors embodied as Pg 13.5 ports, gas connectors for headspace and submerged gassing (to water or media), an exhaust gas connector and a plug connection for exhaust gas cooling, a sampling connector with a sampling valve, for example a swabable valve, a media connector, two dip tubes, a connector for a resistance temperature detector (T or RTD) and a dissolved oxygen (DO) sensor connector having a permeable membrane. A particularly preferred combination of connectors 120 on head plate 100 is shown in FIGS. 5A, 5B, 5C.

Tubes and connection materials which are used with the single-use bioreactor 1 and which can come into contact with reaction media are preferably made of materials with United States Pharmacopeia USP Class VI certification, such as polystyrene, polycarbonate, polyamide or silicone. The tubes to be used are preferably flexible tubes made of thermoplastic elastomers.

The features of the invention which are disclosed in the above description, in the claims and in the drawings may be material in their various embodiments, both separately and in any combination, for realizing the invention.

The invention claimed is:

1. A single-use bioreactor for use in a parallel bioreactor system, for applications in cell culture and/or microbiology, the single-use bioreactor comprising
a head plate, a dimensionally stable container and a mixer, wherein the head plate and the container enclose a reaction chamber, the head plate having an inner side facing towards the reaction chamber, and an outer side which faces away from the reaction chamber and which has a plurality of connectors, and
the mixer having a mixer shaft and a stirring member, the mixer shaft being mounted rotatably about a rotational axis in a bearing and the stirring member being attached torsionally rigidly to the mixer shaft,
wherein the head plate has a convex portion for receiving the bearing, the bearing is designed as a roller bearing and the single-use bioreactor has a bearing housing which defines a bearing chamber for accommodating the bearing inside the reaction chamber, wherein the bearing housing is detachably attached with a fastener to the inner side of the head plate.

2. The single-use bioreactor according to claim 1, wherein the roller bearing comprising a polymer roller bearing with glass ball bearings, and the polymer roller bearing comprising a thermoplastic plastic ball race.

3. The single-use bioreactor according to claim 1, wherein the head plate and the container are permanently joined to each other, the head plate being formed of a first material and the container of a second material, and the mixer shaft and/or the stirring member being formed of a third material, the first material and the second material having a higher temperature resistance than the third material.

4. The single-use bioreactor according to claim 1, wherein the head plate and the container are bonded or welded to each other through ultrasonic welding or infrared welding.

5. The single-use bioreactor according to claim 1, wherein the head plate is of integral construction, wherein the head plate is manufactured in an injection molding process and has a plurality of dip tubes on its inner side which project into the reaction chamber.

6. The single-use bioreactor according to claim 1, wherein the mixer and the bearing are arranged entirely within the reaction chamber and the mixer shaft has a magnetic portion which is arranged and adapted in such a way that it can be coupled magnetically in an axial direction to a rotary drive.

7. The single-use bioreactor according to claim 6, wherein the magnetic portion consists of a composite material comprising a plastic matrix and a magnetic material, or includes such a composite material.

8. The single-use bioreactor according to claim 6, wherein the magnetic portion has a cross-section in a plane which is orthogonal to the mixer shaft, and exerts a magnetic force over the major part of said cross-section for a magnetic coupling to a rotary drive in the axial direction.

9. The single-use bioreactor according to claim 8, wherein the major part of said cross-section comprises the entire cross-section.

10. The single-use bioreactor according to claim 1, wherein the mixer includes a rotor and wherein the roller bearing is configured to accommodate a rotor speed of more than 1500 rotations per minute (rpm).

11. The single-use bioreactor according to claim 1, wherein the fastener comprises a snap-on, clip or screw.

12. A single-use bioreactor, for use in a parallel bioreactor system, for application in cell culture and/or microbiology, the single-use bioreactor comprising:
a head plate; a dimensionally stable container; and a mixer,
wherein the head plate and the container enclose a reaction chamber,
the head plate having an inner side facing towards the reaction chamber, and an outside which faces away from the reaction chamber and which has a plurality of connectors, and
the mixer having a mixer shaft and a stirring member, the mixer shaft being mounted rotatably about a rotational axis in a bearing and the stirring member begin attached torsionally rigidly to the mixer shaft,
wherein the head plat has a convex portion for receiving the bearing, the bearing is designed as a roller bearing and the single use-bioreactor has a bearing housing which delineates a bearing chamber for accommodating the bearing inside the reaction chamber, and
wherein the bearing housing is permanently joined to the inner side of the head plate by ultrasonic welding.

* * * * *

UNITED STATES PATENT AND TRADEMARK OFFICE
CERTIFICATE OF CORRECTION

PATENT NO. : 10,030,220 B2
APPLICATION NO. : 14/408069
DATED : July 24, 2018
INVENTOR(S) : Matthias Arnold et al.

Page 1 of 1

It is certified that error appears in the above-identified patent and that said Letters Patent is hereby corrected as shown below:

In the Claims

Column 16, Line 42-43:
"axis in a bearing and the stirring member begin attached torsionally rigidly to the mixer shaft," should read -- axis in a bearing and the stirring member being attached torsionally rigidly to the mixer shaft, --

Column 16, Line 44:
"wherein the head plat has a convex portion..." should read -- wherein the head plate has a convex portion --

Signed and Sealed this
Nineteenth Day of March, 2019

Andrei Iancu
*Director of the United States Patent and Trademark Office*